US011975072B2

(12) United States Patent
Azais et al.

(10) Patent No.: US 11,975,072 B2
(45) Date of Patent: May 7, 2024

(54) PYROPHEOPHORBIDE CONJUGATE AND USE THEREOF IN THE TREATMENT OF CANCER AND AS A FLUORESCENT MARKER

(71) Applicants: INSERM (INSTITUT NATIONAL DE LA SANTÉ ET DE LA RECHERCHE MÉDICALE), Paris (FR); UNIVERSITE DE LILLE, Lille (FR); CENTRE NATIONAL DE LA RECHERCHE SCIENTIFIQUE, Paris (FR); UNIVERSITE DE LORRAINE, Nancy (FR); INSTITUT PASTEUR DE LILLE, Lille (FR); CENTRE HOSPITALIER REGIONAL UNIVERSITAIRE DE LILLE, Lille (FR)

(72) Inventors: Henri Azais, Lille (FR); Pierre Collinet, Lambersart (FR); Nadira Delhem-Fellahi, Marcq-en-Baroeul (FR); Olivier Morales, Lille (FR); Serge Mordon, Mouvaux (FR); Céline Frochot, Malzeville (FR); Régis Vanderesse, Sexey les Bois (FR); Aurélie Stallivieri, Caen (FR)

( * ) Notice: Subject to any disclaimer, the term of this patent is extended or adjusted under 35 U.S.C. 154(b) by 763 days.

(21) Appl. No.: 16/632,649

(22) PCT Filed: Jul. 20, 2018

(86) PCT No.: PCT/EP2018/069836
§ 371 (c)(1),
(2) Date: Jan. 21, 2020

(87) PCT Pub. No.: WO2019/016397
PCT Pub. Date: Jan. 24, 2019

(65) Prior Publication Data
US 2022/0378914 A1    Dec. 1, 2022

(30) Foreign Application Priority Data

Jul. 21, 2017 (FR) .................................... 1756924

(51) Int. Cl.
*A61K 41/00*    (2020.01)
*A61K 47/54*    (2017.01)
*A61K 49/00*    (2006.01)
*A61P 35/00*    (2006.01)

(52) U.S. Cl.
CPC ........ *A61K 41/0071* (2013.01); *A61K 47/546* (2017.08); *A61K 49/0052* (2013.01); *A61P 35/00* (2018.01)

(58) Field of Classification Search
CPC ............. A61K 41/0071; A61K 47/546; A61K 49/0052; A61P 35/00
See application file for complete search history.

(56) References Cited

U.S. PATENT DOCUMENTS

2012/0059018 A1    3/2012    Park et al.

FOREIGN PATENT DOCUMENTS

| CN | 102895670 A | 1/2013 |
| CN | 106279212 A | 1/2017 |
| EP | 2431366 A1 | 3/2012 |
| WO | 2004005289 A2 | 1/2004 |
| WO | 2007042775 A2 | 4/2007 |

OTHER PUBLICATIONS

The English translation of the Chinese Office Action, dated Aug. 1, 2022, in the related Chinese Patent Application No. 201880060640.8.
The English translation of the Japanese Office Action, dated May 16, 2022, in the related Japanese Patent Application No. 2020-524684.
The English translation of the International Search Report and Written Opinion, dated Sep. 20, 2018, in the corresponding PCT Appl. No. PCT/EP2018/069836.
You Hyun et al: "Pheophorbide-aconjugates with cancer-targeting moieties for targeted photodynamic cancer therapy", Bioorganic & Medicinal Chemistry, Pergamon, GB, vol. 23, No. 7, Feb. 16, 2015, pp. 1453-1462, XP029204983.
Schneider R et al: "Design, synthesis, and biological evaluation of folic acid targeted tetraphenylporphyrin as novel photosensitizers for selective photodynamic therapy", Bioorganic & Medicinal Chemistry, Pergamon, GB, vol. 13, No. 8, Apr. 15, 2005, pp. 2799-2808, XP027637588.

*Primary Examiner* — Robert S Cabral

(57) ABSTRACT

The invention relates to a compound of formula (I) and to the pharmaceutically acceptable salts thereof. The invention also relates to the use of said compound of formula (I) in the treatment of cancer, particularly by photodynamic therapy.

Figure 1:
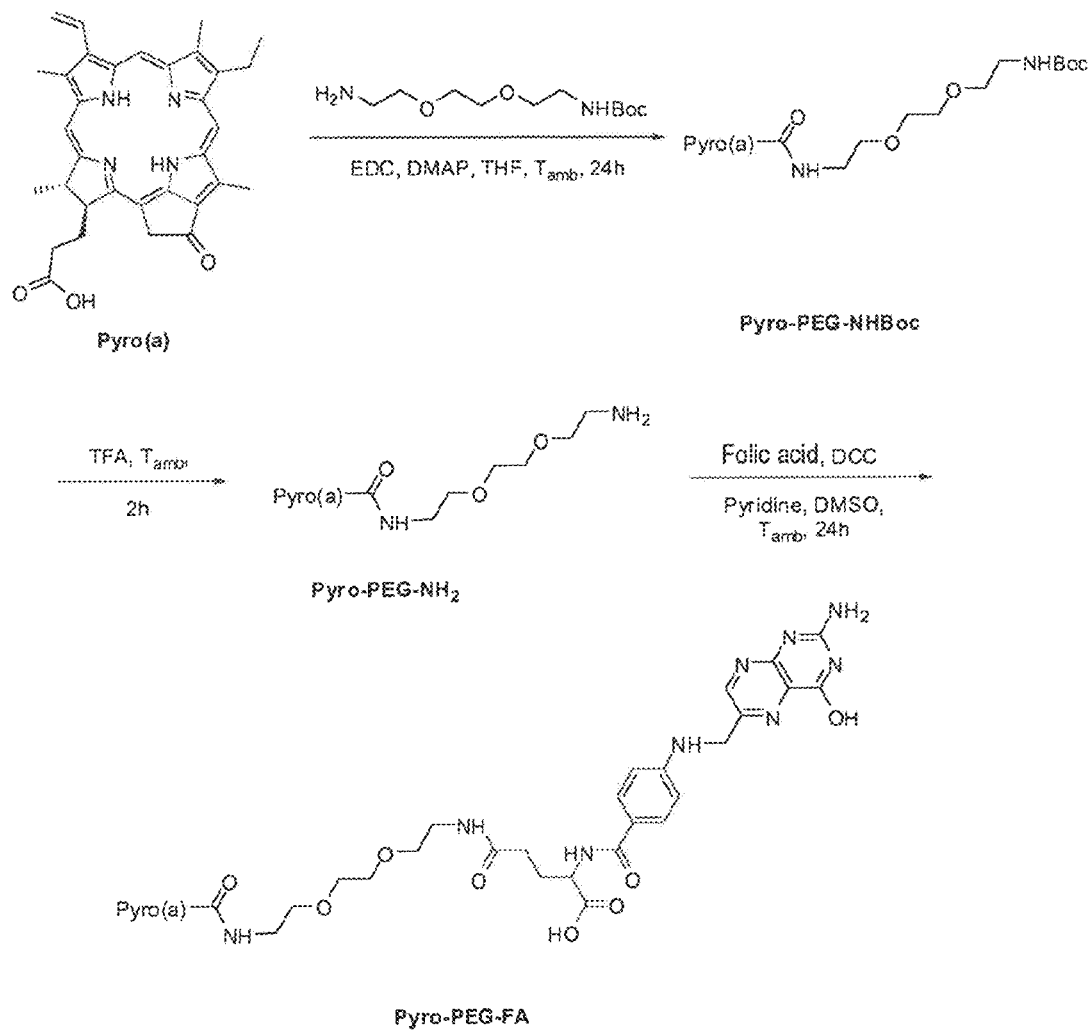

12 Claims, 5 Drawing Sheets
Specification includes a Sequence Listing.

PYROPHEOPHORBIDE CONJUGATE AND USE THEREOF IN THE TREATMENT OF CANCER AND AS A FLUORESCENT MARKER

CROSS-REFERENCE TO RELATED APPLICATIONS

This application is a National Stage Application of PCT/EP2018/069836 filed Jul. 20, 2018, which claims priority from French Patent Application No. 1756924 filed Jul. 21, 2017. Each of the prior mentioned applications is hereby incorporated by reference herein in its entirety.

REFERENCE TO AN ELECTRONIC SEQUENCE LISTING

The instant application contains a Sequence Listing which has been submitted in ASCII format and is herein incorporated by reference in its entirety. Said ASCII copy, created on Sep. 20, 2021, is named 2021-09-20_SequenceListing_102642.txt and is 3 KB in size.

The present invention relates to the field of photosensitizers and, more particularly, to the uses thereof in photodynamic therapy protocols for treating a cancer, in particular an ovarian cancer.

TECHNICAL BACKGROUND OF THE INVENTION

Ovarian cancer represents 4500 new cases each year in France. The poor prognosis of the disease is linked to the delay in diagnosis since the majority of cases are diagnosed at stages III and IV of the International Federation of Gynecology and Obstetrics (FIGO), and the survival rate decreases with the progression of the disease. Ovarian cancer is responsible for the majority of deaths due to gynecological cancer in the United States and in Western Europe. Approximately 3500 deaths are attributed thereto each year in France.

The disease frequently progresses to the appearance of metastases in the form of peritoneal carcinomatosis, which corresponds to the presence of numerous tumors at the surface of the organs of the abdominopelvic cavity. The peritoneum is a continuous serous membrane (formed by a single layer of mesothelial cells) which coats the abdomen, the pelvis and the viscera, delimiting the virtual space of the peritoneal cavity. A distinction is made between the visceral peritoneum (which coats the exterior of the organs) and the parietal peritoneum (which coats the internal face of the walls of the abdomen).

Current therapy combines, when it is possible, surgery with chemotherapy based on the use of platinum salts, and in certain cases with targeted therapies. It is accepted that the absence of residual lesions after surgery is the principal factor of a good prognosis. The capacity of the surgical treatment to eradicate all of the tumor implants is thus decisive. Systemic adjuvant or neo-adjuvant chemotherapy has enabled an improvement in the survival rates to five years, especially in the early stages: 81% for stages I and II after three cycles of chemotherapy combining carboplatin and paclitaxel. In the context of a maximum cytoreduction and as a supplement to macroscopically complete tumor reduction surgery, therapeutic strategies can be envisioned, such as intraperitoneal chemotherapy and intraperitoneal photodynamic therapy. Despite numerous clinical trials, the benefit of intraperitoneal chemotherapy has not been demonstrated in this indication and this option is not recommended outside a clinical trial.

Contrary to intraperitoneal chemotherapy, with or without hyperthermia, recourse to a photosensitizer selectively targeting the early lesions, and only these lesions, would make it possible to reduce the toxicity of the treatment, since the action of the light takes place only in the presence of photosensitizers within the tumor tissue. It could also make it possible to treat the microscopic metastases that are ignored during surgery. Thus, recourse to more specific photosensitizers targeting receptors overexpressed by ovarian tumor cells could reinforce the efficacy of photodynamic therapy (PDT).

In this context, Schneider et al. (Bioorganic & Medicinal Chemistry, 2005, 13, 2799-2808) have synthesized a photosensitizer comprising a triphenylporphyrinyl unit conjugated with folic acid (TPP-FA) having both fluorescent properties and antiproliferative properties that are advantageous for application in photodynamic therapy. More particularly, Azaïs et al. (Photodiagnosis and Photodynamic Therapy, 2016, 13, 130-138) have demonstrated on an animal model that this photosensitizer is in particular specific for peritoneal metastases of ovarian epithelial cancers and have thus suggested the use thereof in the development of intraperitoneal photodynamic therapy protocols not toxic to the patient. However, this photosensitizer exhibits, on the one hand, very weak fluorescence thus preventing its detection with the medical devices commonly used by gynecologists and, on the other hand, low stability.

You et al. (Bioorganic & Medicinal Chemistry, 2015, 23, 1453-1462) have also developed pheophorbide-a conjugates, in particular a photosensitizer comprising a pheophorbide-a unit conjugated with folic acid via a spacer arm of polyethylene glycol type (Pheo-PEG-FA). You et al. have in particular shown that this photosensitizer (Pheo-PEG-FA) targets folate receptors and can thus be used in photodynamic therapy protocols for treating cancers overexpressing folic acid receptors with a view to its fluorescent properties. However, this photosensitizer exhibits relatively moderate fluorescence.

Thus, there is at the current time a real need to develop new photosensitizers to be used in photodynamic therapy. These photosensitizers must both have good therapeutic efficacy and selectively target the lesions so as not to damage the healthy tissues, and must have sufficient fluorescence in order to visualize these lesions by means of medical devices.

SUMMARY OF THE INVENTION

In the face of this problem, the inventors have synthesized, by means of a process guaranteeing excellent yields, a new photosensitizer comprising a pyropheophorbide-a unit conjugated with folic acid via a spacer arm of polyethylene glycol type (Pyro-PEG-FA). The analysis of this photosensitizer has made it possible to demonstrate improved physicochemical properties compared with the structurally similar conjugates described above and also good light-stability. The inventors have also demonstrated that this new photosensitizer makes it possible to specifically target the microscopic peritoneal metastases of ovarian epithelial cancers without impairing the quality of the antitumor effector immune response.

The present invention thus relates to a compound of formula (I):

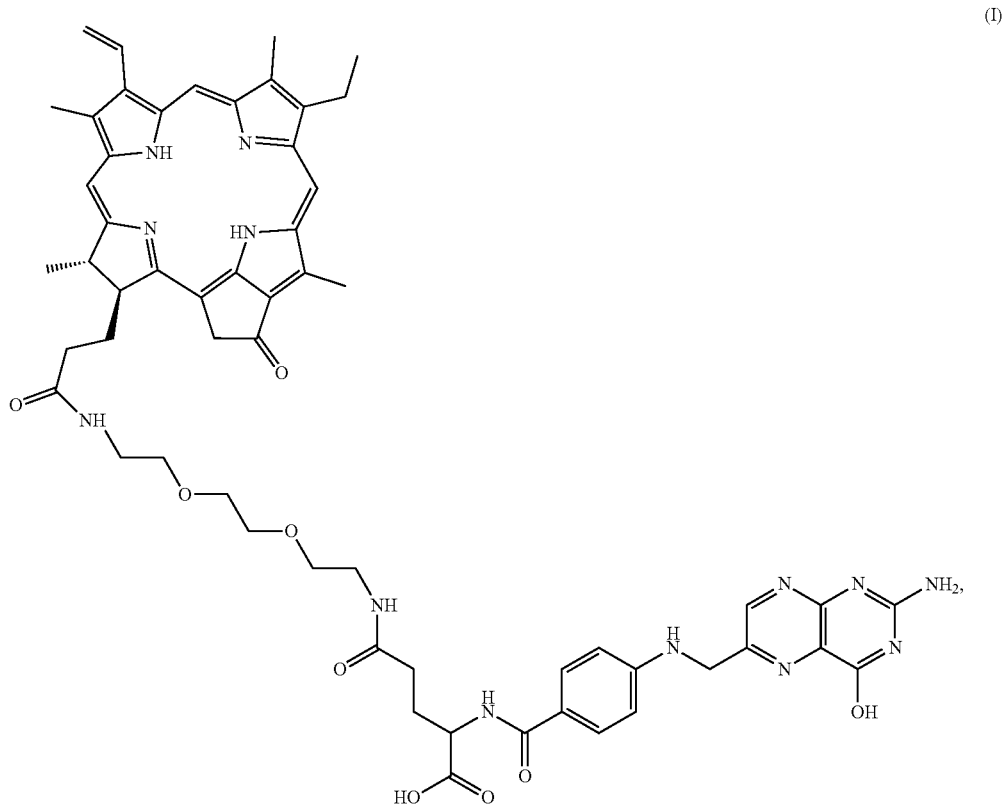 [SMILES: C=Cc1c(C)c2cc3nc(c4c5[nH]c(cc6nc(cc1[nH]2)C(C)=C6CC)c(C)c5C(=O)C4)[C@@H](CCC(=O)NCCOCCOCCNC(=O)CCC(NC(=O)c1ccc(NCc2cnc4nc(N)nc(O)c4n2)cc1)C(=O)O)[C@@H]3C]

(I)

and the pharmaceutically acceptable salts thereof.

The invention also relates to the use of this compound of formula (I) as a medicament.

According to one particular embodiment of the invention, the compound of formula (I) is used for the treatment of a cancer, and in particular by photodynamic therapy. In particular, the compound of formula (I) of the invention is used for reducing the risk of developing metastases. Preferably, the compound of formula (I) is used for the treatment of a cancer chosen from ovarian, lung, kidney, endometrial, colorectal or breast cancer, pancreatic cancer, brain, gastric, liver, prostate, testicular, bladder, or head and neck cancer. More preferentially, the compound of formula (I) is used for the treatment of ovarian cancer.

According to another particular embodiment, the compound of formula (I) is intended to be administered intraperitoneally or intravenously.

Another subject of the invention relates to a process for preparing a compound of formula (I) as represented above, comprising a step of coupling between a compound of formula (II):

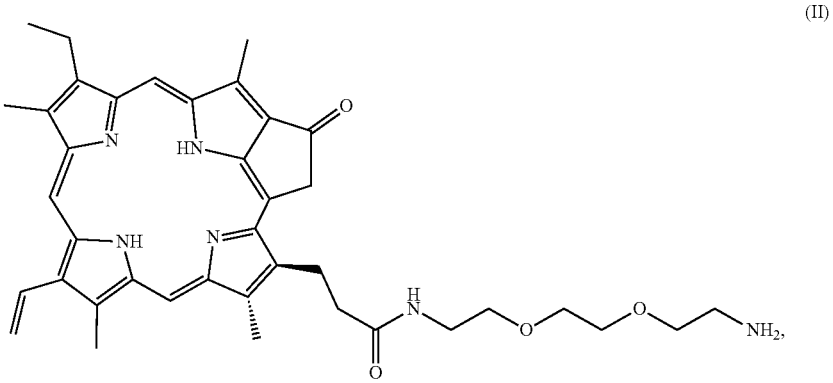

(II)

and folic acid.

Another subject of the invention also relates to a use of the compound of formula (I) as represented above as a fluorescent marker.

Another subject of the invention also relates to a method for imaging in a subject, comprising the visualization of the fluorescence emitted by a compound of formula (I) previously administered to said subject and photoactivated by a light source.

FIGURE LEGENDS

FIG. 1: Process for synthesizing the Pyro-PEG-FA compound of formula (I).

Figure 2:
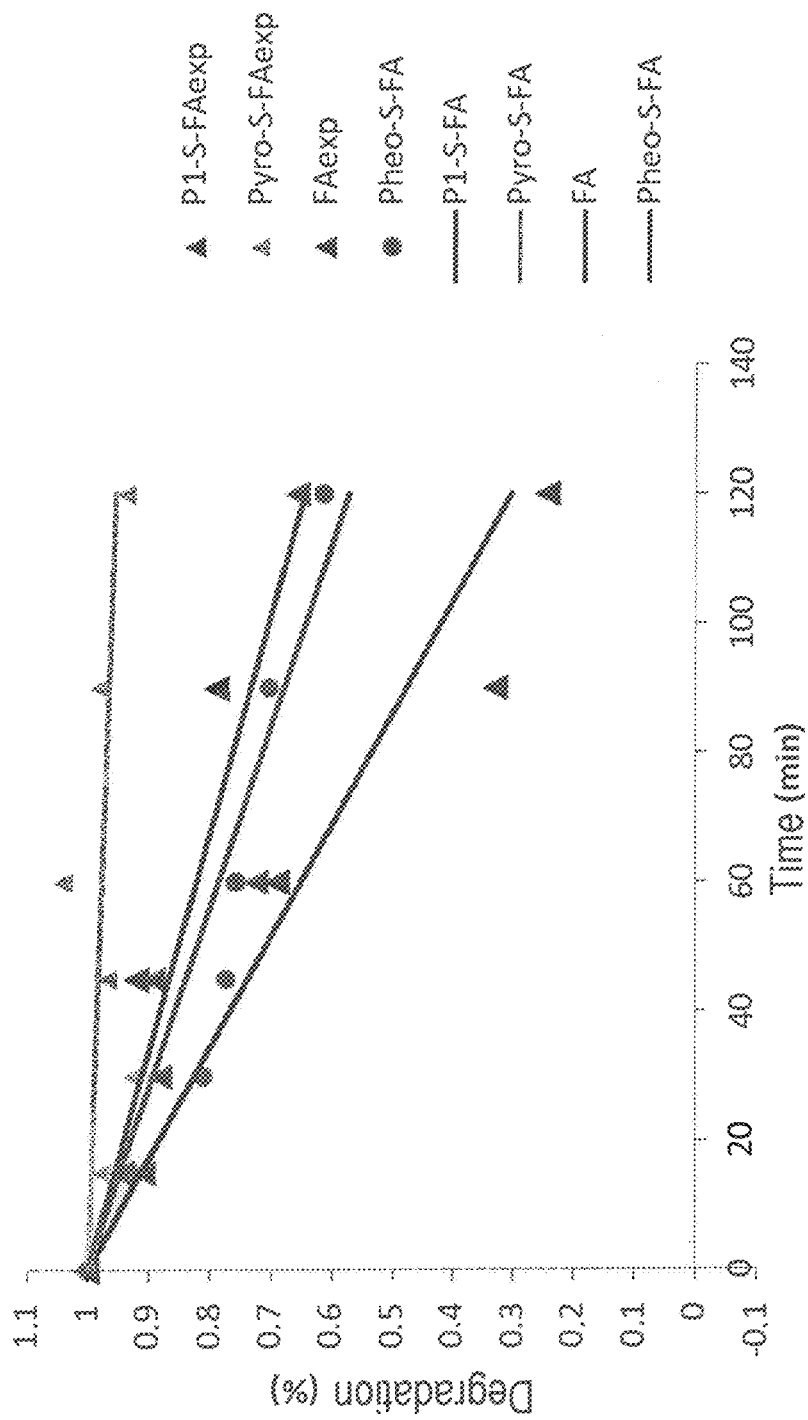

FIG. 2: Photodegradation of folic acid (FA), of the Pyro-PEG-FA compound of formula (I) (Pyro-S-FA), of the Pheo-PEG-FA compound (Pheo-S-FA), and of the TPP-FA compound (P1-S-FA) over time (365 nm, 5 mW/cm$^2$, [0.45 mM] in DMSO).

Figure 3A:
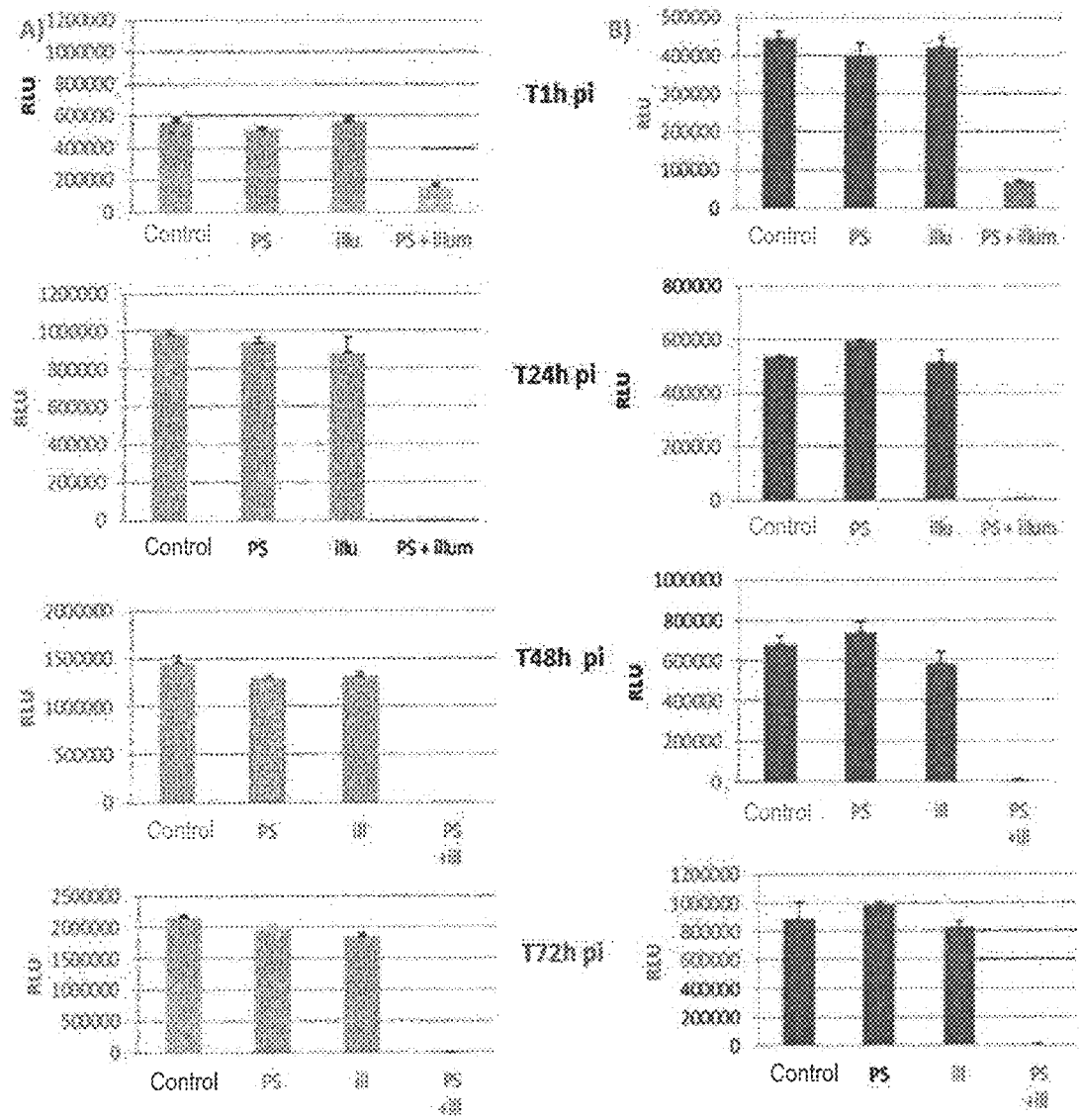

FIG. 3A: Measurement of the relative amount of ATP in the SKOV-3 (A) and OVCAR-3 (B) ovarian tumor cells subjected to the PDT.

Figure 3B:
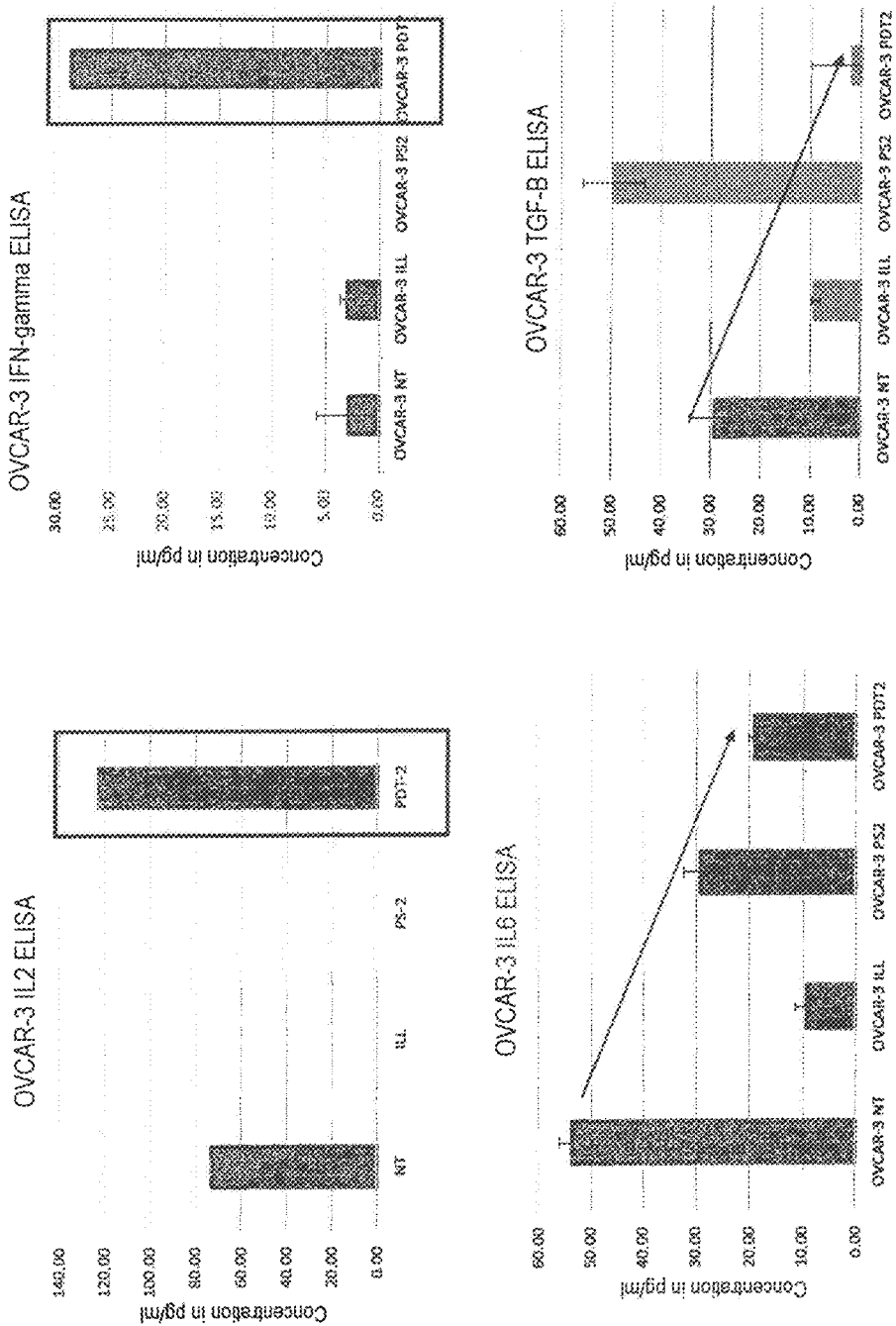

FIG. 3B: Impact of the PDT on the cytokine secretion by the OVCAR-3 ovarian tumor cells.

Figure 4A:
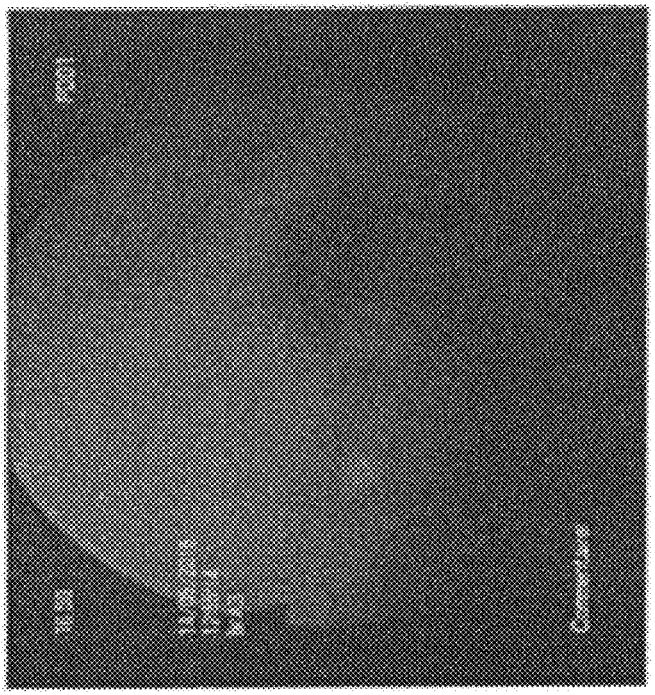

FIG. 4A: Photograph of a celioscopy image in an immunocompetent rat having developed a peritoneal carcinomatosis after injection of the Pyro-PEG-FA compound of formula (I).

Figure 4B:
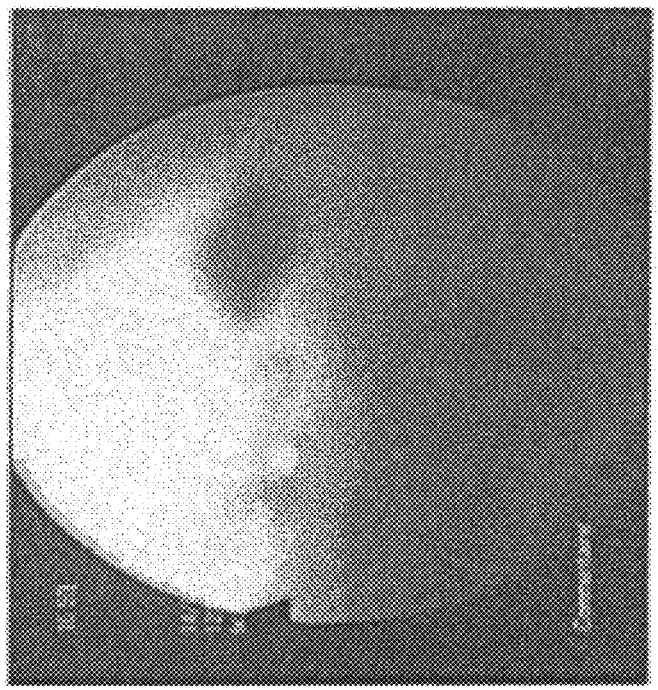

FIG. 4B: Photograph of FIG. 4A in white light.

DETAILED DESCRIPTION OF THE INVENTION

As illustrated and demonstrated by the inventors in the examples below, the present invention provides a new photosensitizer coupled to a folate of formula (I):

i) making it possible to specifically target the microscopic peritoneal metastases of ovarian epithelial cancers,
ii) having good therapeutic efficacy,
iii) offering sufficient fluorescence to visualize the lesions by means of conventional medical devices,
iv) requiring few steps for its synthesis, and
v) activating immune cell proliferation.

Pyro-PEG-FA Compound of Formula (I)

The present invention thus relates to a compound of formula (I):

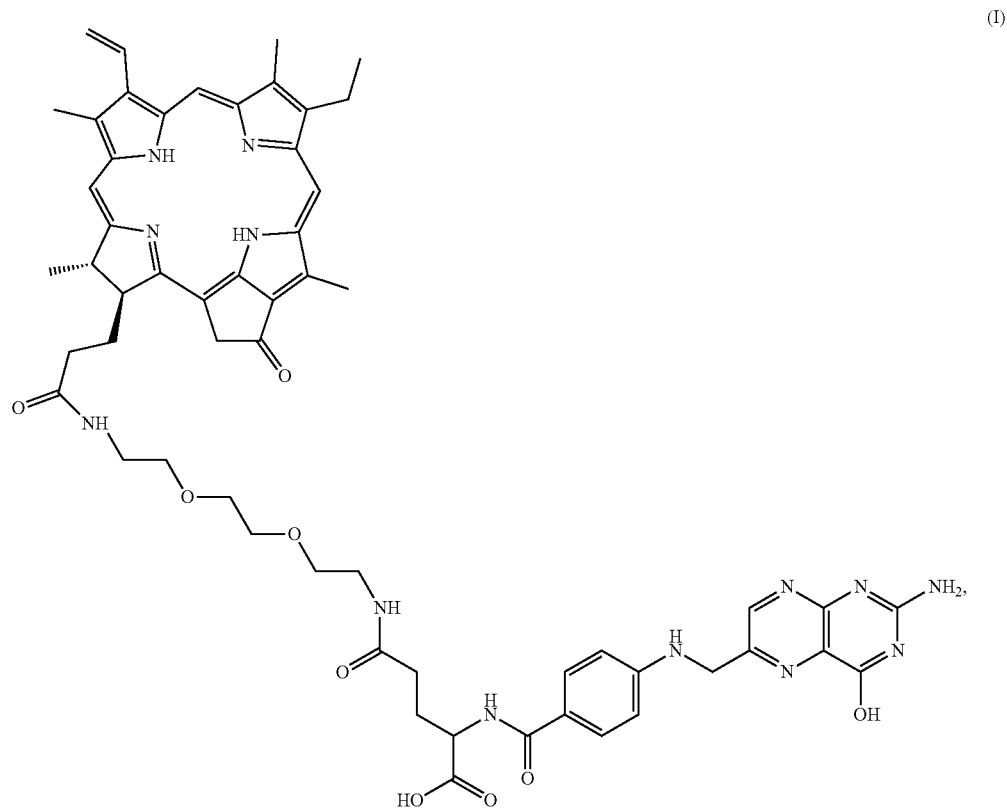 [SMILES: C=Cc1c(C)c2cc3nc(c4c5[nH]c(cc6nc(cc1[nH]2)C(C)=C6CC)c(C)c5C(=O)C4)[C@@H](CCC(=O)NCCOCCOCCNC(=O)CCC(NC(=O)c1ccc(NCc2cnc4nc(N)nc(O)c4n2)cc1)C(=O)O)[C@@H]3C]

and the pharmaceutically acceptable salts thereof.

This compound of formula (I) is a conjugated compound comprising a pyropheophorbide-a unit conjugated with folic acid via a spacer arm of polyethylene glycol type (Pyro- PEG-FA). The pyropheophorbide-a unit gives the compound of formula (I) satisfactory fluorescence for visualizing the lesions. The spacer arm of polyethylene glycol type comprises two monomers of polyethylene glycol $PEG_2$. The folic acid unit makes it possible to specifically target folic acid receptors. In the present description, the compound of formula (I) is represented by "Pyro-PEG-FA" or "Pyro-$PEG_2$-FA".

The expression "pharmaceutically acceptable salt(s) thereof" denotes the salts of the compound of interest of formula (I) which have the desired biological activity. The pharmaceutically acceptable salts comprise salts of acidic or basic groups present in the specified compound. The pharmaceutically acceptable acid addition salts comprise, but are not limited to, hydrochloride, hydrobromide, hydriodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate and p-toluenesulfonate salts and the pamoate salt (that is to say, 1,1'-methylenebis(2-hydroxy-3-naphthoate)). Suitable base salts comprise, but are not limited to, aluminum, calcium, lithium, magnesium, potassium, sodium, zinc and diethanolamine salts. A list of pharmaceutically acceptable salts is in particular published in the review by Berge et al. (J. Pharm. Sci. 1977, 66(1), 1-19).

The compound of formula (I) can be synthesized by means of a simple process comprising a step of coupling between a compound of formula (II):

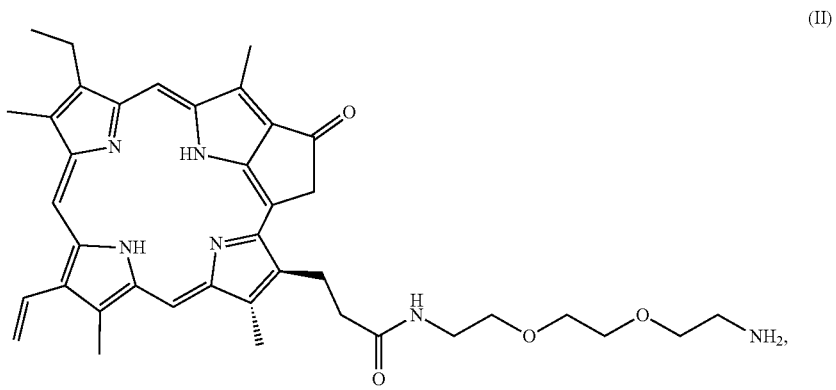

(II)

and folic acid.

More particularly, the compound of formula (I) can be synthesized by means of a process comprising three steps starting from the pyropheophorbide-a of formula (IV) as sold by the company Boc sciences. According to one preferred embodiment, the compound of formula (I) is prepared by means of a process comprising the following steps:

(a) a step of coupling between a compound of formula (IV):

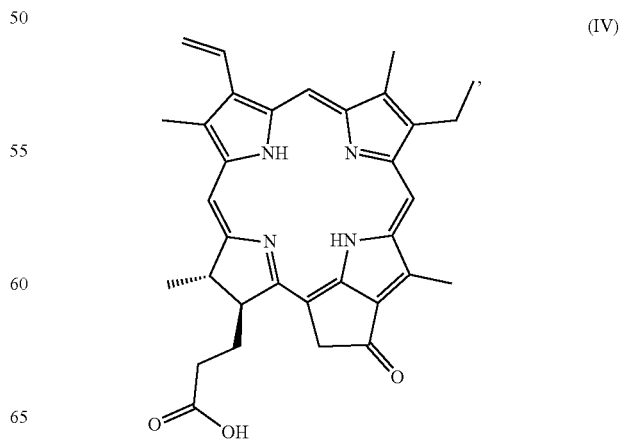

(IV)

and N-Boc-2,2'-(ethylenedioxy)diethylamine, so as to obtain a compound of formula (III):
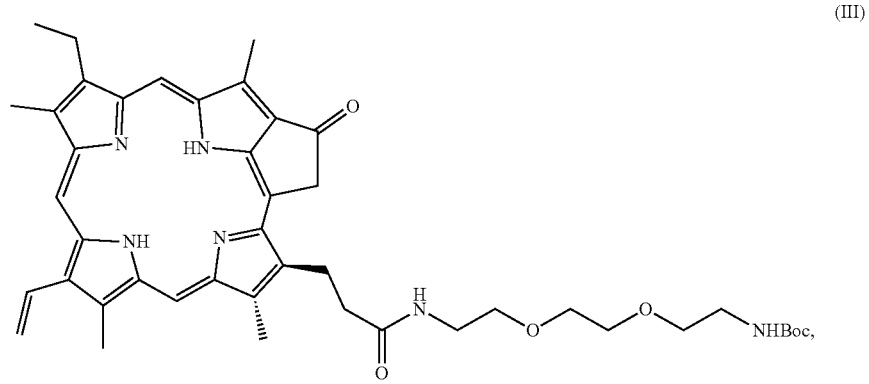
(III)
b) a step of deprotection of the compound of formula (III) obtained in step a) so as to obtain a compound of formula (II):
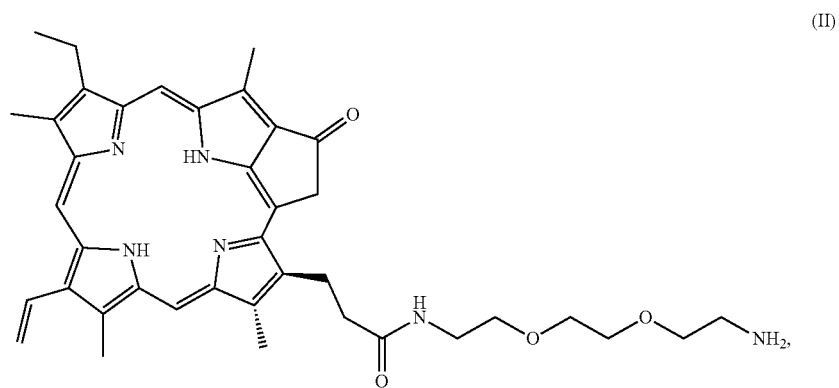
(II)
and
c) a step of coupling between the compound of formula (II) obtained in step b) and folic acid so as to obtain a compound of formula (I):

(I)

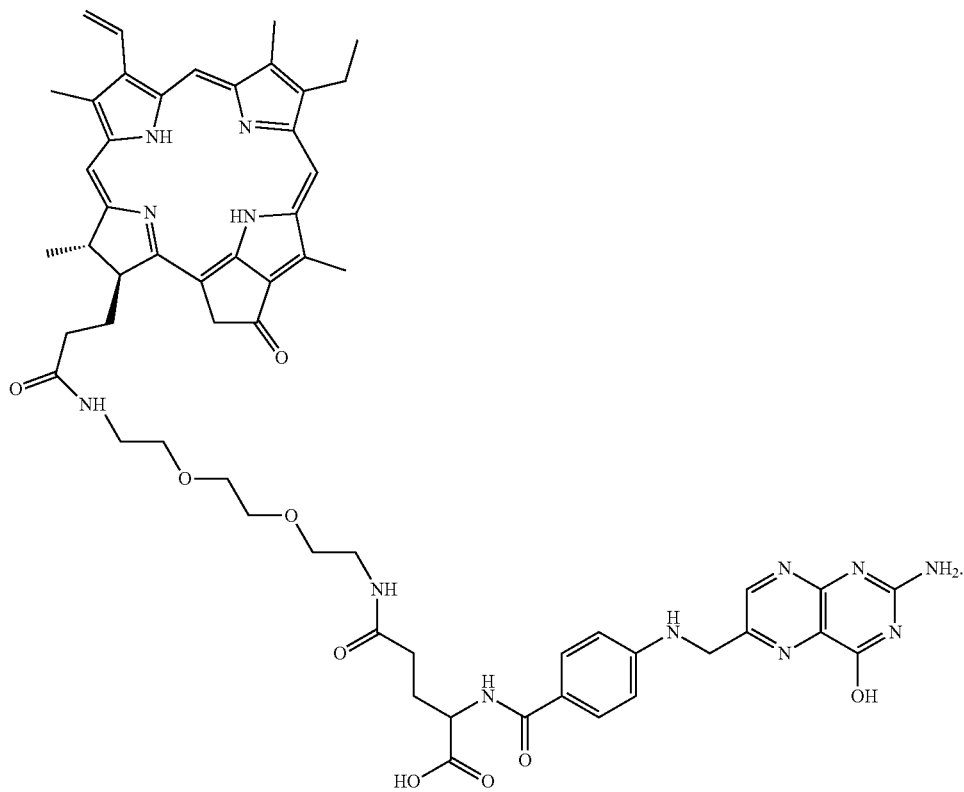

This simple process which requires only three steps makes it possible to obtain the compound of formula (I) with very satisfactory yields, which are in particular higher compared with the yields obtained by means of the process using the compound of You et al. (Pheo-PEG-FA). This process is thus more advantageous and is appropriate for industrial application.

Application

The compound of formula (I) as described above can be used as a medicament, preferably in the treatment of cancer.

For the purposes of the present invention, the terms "treatment" and "treating" denote an improvement, the prophylaxis or the reversal of a disease or of a disorder, in the case in point a cancer. The term "treatment of a cancer" is intended to mean equally the reduction of the number of metastases and/or the reduction of the risk of developing metastases. In the context of the treatment of metastases, the objective is in particular to reduce the rate of recurrence or of relapse for the patient in terms of developing a cancer. The term "treatment of a cancer" is also intended to mean the inhibition of cancer cell proliferation.

Without wishing to be bound to a particular mechanism of action, the compound of formula (I) makes it possible to activate the immune system, thus contributing to combating the cancer. Thus, it is proposed to use the compound of formula (I) according to the invention in the treatment of cancer by immunotherapy, in particular by activation of the immune system after photodynamic treatment.

More particularly, the compound of formula (I) is used in the treatment of cancer by photodynamic therapy.

Photodynamic therapy, commonly referred to by the acronym PDT, consists in bringing a pathological tissue into contact with a photoactivatable molecule (referred to as photosensitizer or photosensitizing agent), in the case in point the compound of formula (I) in the context of the present invention, then in illuminating this tissue with a light having a wavelength (color) appropriate for the activation characteristics of the photosensitizer. After activation of the molecule by the light and reaction with the oxygen of the tissue, very toxic species are produced locally so as to ultimately induce the destruction of the cancer lesion. The major advantage of PDT is its selectivity. Indeed, the light used is not on its own harmful; the photosensitizer without light is not toxic. To induce the reaction, a combined action of the light, of the photosensitizer and of oxygen is necessary. Thus, by optimizing the photosensitizer concentration and the light dose, it is possible to selectively destroy cells.

Thus, the invention also relates to a compound of formula (I) as described above, for use thereof in the treatment of cancer, wherein an effective dose of the compound of formula (I) is brought into contact with the cancer cells and/or the metastases which are subsequently exposed to a light source.

The invention also relates to a method for treating a cancer, comprising the steps of bringing the cancer cells into contact with an effective dose of the compound of formula (I) as described above, and exposing the cancer cells to a light source.

The term "effective dose" is intended to mean a dose sufficient to obtain satisfactory fluorescence and to thus obtain the desired therapeutic effect. Those skilled in the art are capable of adjusting this dose as a function of the severity and of the type of cancer to be treated. Nevertheless, an effective dose of the compound of formula (I) may be comprised between 0.1 mg/kg and 100 mg/kg, between 0.1 mg/kg and 50 mg/kg, between 0.1 mg/kg and 10 mg/kg, preferably between 0.1 mg/kg and 5 mg/kg, and even more preferably between 0.1 mg/kg and 3 mg/kg.

The photoactivation of the photosensitizer, in the case in point the compound of formula (I) in the context of the present invention, can be obtained by any type of light source known to those skilled in the art. In particular, the photoactivation can be carried out by artificial light (lamps, lasers) with radiation such as radiation of ultraviolet or infrared type, or by visible or natural light. The appropriate mode of illumination by means of light devices placed in the cavity of the human body is chosen by those skilled in the art as a function of the type of cancer to be treated. For example, for liver cancer, the light device is placed in the peritoneal cavity. For ovarian cancer, the light device is placed in the pelvic cavity; etc. As nonlimiting examples of light devices, mention may be made of a light balloon as described by Munck et al. (Photodiagnosis and Photodynamic Therapy, 2016, 16, 23-26) or a luminous textile (LEF) as described by Guyon et al. (Journal of Biomedical Optics, 2012, 17(3)).

The wavelength of the light used is chosen so as to obtain the most effective photosensitizer effect. In particular, a wavelength of between 300 and 800 nm, preferably between 400 and 700 nm, and more preferably around 668 nm is used.

The irradiation is generally applied at a dose of between 1 and 200 joules/cm$^2$, preferably between 1 and 150 joules/cm$^2$, and even more preferably around 150 joules/cm$^2$. On cells, a dose of between 1 and 10 joules/cm$^2$ is generally applied.

Preferably, a light source with a light intensity of from 1 to 150 mW/cm$^2$, from 1 to 100 mW/cm$^2$, from 30 to 70 mW/cm$^2$, preferably around 50 mW/cm$^2$ is used. On cells, a light source with a light intensity of from 1 to 10 mW/cm$^2$, or better still of approximately 5 mW/cm$^2$ is used.

The photoactivation of the photosensitizer and the exposure of the cancer cells to a light source can be carried out for a period ranging from 1 minute to 3 hours, 10 minutes to 2 hours, 30 minutes to 90 minutes, preferably for a period of one hour or 60 minutes.

The invention described in the present application is preferentially carried out in human beings.

The compound of formula (I) has a folate unit and can thus be used in the context of treatment by photodynamic therapy for any type of cancer expressing folate receptors. A list of these cancers expressing folate receptors is described by Assaraf et al. (Drug resistance Updates, 2014, 17, 89-95) and includes in particular ovarian, lung, kidney, endometrial, colorectal and breast cancer, pancreatic cancer, brain, gastric, liver, prostate, testicular and bladder cancer, or head and neck cancer.

According to one preferred embodiment of the invention, the cancer is chosen from ovarian, lung, kidney, endometrial, colorectal and breast cancer, pancreatic cancer, brain, gastric, liver, prostate, testicular and bladder cancer, or head and neck cancer. According to an even more preferred embodiment, the cancer is ovarian cancer.

The compound of formula (I) can be administered to the patient by any type of route known to those skilled in the art as a function of the type of cancer to be treated. For example, the intraperitoneal route or the intravenous route can be used for treating ovarian cancer. According to one preferred embodiment of the invention, the compound of formula (I) is intended to be administered intraperitoneally or intravenously, preferably intravenously.

In view of its improved absorption and fluorescence properties, the compound of formula (I) can be used as a fluorescent marker. For example, the compound of formula (I) as a fluorescent marker can be used in the treatment of cancer by fluorescence-guided surgery, and/or in imaging or diagnostic methods.

A method for imaging or for diagnosing a cancer in a subject, comprising the administration to said subject and the irradiation or the photoactivation of a compound of formula (I), and the visualization of the fluorescence emitted, is thus described. This method makes it possible to visualize the folic acid receptors which are overexpressed in cancer cells. This imaging thus makes it possible to delimit the cancer zone and, also, to guide a surgical act of ablation type, where appropriate.

A subject of the invention is thus a method for imaging in a subject, comprising the visualization of the fluorescence emitted by a compound of formula (I) previously administered to said subject and photoactivated by a light source.

In view of its same properties, the compound of formula (I) can also be used as a photosensitizer in cosmetic and dermatological applications, such as photo rejuvenation, treatment of common acne or skin aging.

The present invention thus also relates to a non-therapeutic use of the compound of formula (I) described above, as a photosensitizer.

Other aspects and advantages of the invention will emerge on reading the examples which follow, which should be considered to be illustrative and nonlimiting.

EXAMPLES

Example 1: Synthesis of the Pyro-PEG-FA Conjugate of Formula (I) According to the Invention and of the Pheo-PEG-FA Conjugate of You et al The process for synthesizing the Pyro-PEG-FA conjugate comprising three steps is described below and is also illustrated by FIG. 1.

Step a) Synthesis of Pyro-PEG-NHBoc (Formula III)

100 mg of pyropheophorbide-a (0.19 mmol), 46.4 mg of N-Boc-2,2'-(ethylenedioxy)diethylamine (0.19 mmol), 71.7 mg (0.38 mmol) of EDC and 30.5 mg (0.25 mmol) of DMAP were dissolved in 30 ml of THF. The reaction mixture was stirred at ambient temperature, under a nitrogen atmosphere and in the dark for 24 hours. The solvent was then evaporated off. The crude material was purified on a silica gel chromatography column with 5% of EtOH in $CH_2Cl_2$. The Pyro-PEG-NHBoc compound is obtained in the form of a dark green solid with a yield of 92% (132 mg). Rf=0.27 ($CH_2Cl_2$/EtOH=95/5, v/v). $^1$H NMR (300 MHz, DMSO-d6): δ (ppm)=−2.01 (s, 2H, NH, Pyro(a)-COOH), 1.30 (s, 9H, Boc), 1.60 (t, 3H, $CH_3$, Pyro(a)-COOH), 1.79 (d, 3H, $CH_3$, Pyro(a)-COOH), 2.98 (q, 2H, $CH_2$), 3.15, 3.35, 3.59 (3×s, 3H×3, $CH_3$, Pyro(a)-COOH), 3.46 (q, 2H, $CH_2$), 3.60 (m, 8H, $CH_2$), 3.65 (m, 2H, $CH_2$, Pyro(a)-COOH), 4.31, 4.56 (2×d, 1H×2, CH, Pyro(a)-COOH), 5.16 (q, 2H, $CH_2$, Pyro(a)-COOH), 6.34, 6.40 (2×d, 1H×2, =$CH_2$, Pyro(a)-COOH), 6.66 (s, 1H, NH-spacer), 7.83 (t, 1H, NH-spacer), 8.19 (q, 1H, —CH=, Pyro(a)-COOH), 8.88, 9.38, 9.65 (3×s, 1H×3, CH, Pyro(a)-COOH). HRMS (ESI+): m/z calc. for $C_{44}H_{56}N_6O_6$ [M+H]+ 765.4334; found 765.4304.

Step b) Synthesis of Pyro-PEG-NH$_2$ (Formula II)

The Pyro-PEG-NHBoc compound was dissolved in 2 ml of TFA. The solution was stirred for 2 hours at ambient temperature in the dark and under nitrogen and then freeze-dried in order to remove the TFA. The colored residue was dissolved in CH$_2$Cl$_2$ (10 ml), and anhydrous potassium carbonate was added until the color changed from blue to green. After filtration, the organic phase was concentrated. The crude material was purified on a silica gel chromatography column with CH$_2$Cl$_2$/EtOH (from 90:10 to 50:50, v/v), giving Pyro-PEG-NH$_2$ (103 mg, 90%) in the form of a green solid. Rf=0.17 (CH$_2$Cl$_2$/EtOH=1:1, v/v). $^1$H NMR (300 MHz, DMSO-d6): δ (ppm)=−1.94 (s, 2H, NH, Pyro(a)-COOH), 1.63 (t, 3H, CH$_3$, Pyro(a)-COOH), 1.79 (d, 3H, CH$_3$, Pyro(a)-COOH), 2.87 (t, 2H, CH$_2$), 3.17 (q, 2H, CH$_2$), 3.23-3.62 (3×s, 3H×3, CH$_3$, Pyro(a)-COOH), 3.50 (s, 8H, CH$_2$), 3.71 (m, 2H, CH$_2$, Pyro(a)-COOH), 4.30, 4.58 (2×d, 1H×2, CH, Pyro(a)-COOH), 5.17 (q, 2H, CH$_2$, Pyro(a)-COOH), 6.22, 6.39 (2×d, 1H×2, =CH$_2$, Pyro(a)-COOH), 7.98 (t, 1H, NH), 8.18 (s, 2H, NH$_2$), 8.24 (q, 1H, —CH=, Pyro(a)-COOH), 8.90, 9.45, 9.73 (3×s, 1H×3, C20-10-5, Pyro(a)-COOH). HRMS (ESI+): m/z calc. for C$_{39}$H$_{48}$N$_6$O$_4$ [M+H]+ 665.3810; found 665.3801.

Step c) Synthesis of Pyro-PEG-FA (Formula I)

Folic acid (0.95 eq., 63 mg) and DCC (1 eq., 31 mg) were dissolved in a mixture of anhydrous DMSO (5 ml) and pyridine (2 ml). The mixture was stirred for 15 min at ambient temperature, in the dark and under nitrogen. Pyro-PEG-NH$_2$ (0.9 eq.) was then added and the reaction mixture was stirred for 24 h at ambient temperature. The solution was slowly poured into vigorously stirred cold diethyl ether (45 ml). The precipitate obtained was collected by centrifugation and washed with diethyl ether (50 ml). The Pyro-PEG-FA powder was vacuum-dried (107 mg, 69%). $^1$H NMR (300 MHz, DMSO-d6): −1.97 (s, 2H, NH, Pyro(a)-COOH), 1.62 (t, 3H, C8: CH$_3$, Pyro(a)-COOH), 1.76 (d, 3H, C18: CH$_3$, Pyro(a)-COOH), 4.32 (2H, CH+C17, FA+Pyro(a)-COOH), 4.40 (d, 2H, CH$_2$, FA), 4.56 (d, 1H, C18, Pyro(a)-COOH), 5.17 (q, 2H, C13: CH$_2$, Pyro(a)-COOH), 6.21, 6.50 (2×d, 1H×2, C3: =CH$_2$, Pyro(a)-COOH), 6.60 (d, 2H, CHarom., FA), 7.29 (br, 3H, NH+NH$_2$), 7.61 (d, 2H, CHarom., FA), 7.81 (s, 2H, NH$_2$), 7.92 (d, 1H, NH, FA), 8.20 (q, 1H, C3: —CH=, Pyro(a)-COOH), 8.59 (d, 1H, CHarom., FA), 8.88, 9.42, 9.68 (3×s, 1H×3, C20-10-5, Pyro(a)-COOH). HRMS (ESI+): m/z calc. for C$_{58}$H$_{65}$N$_{13}$O$_9$ [M+Na]+ 1110.4920; found 1110.4872.

The conjugate of You et al. (Pheo-PEG-FA) was synthesized according to the same three-step process described above. The yields obtained for each of the three steps are described in table 1 below.

TABLE 1

| Compound | Price | Yld step a) | Yld step b) | Yld step c) | Total Yld |
|---|---|---|---|---|---|
| Pheo-PEG-FA (You et al.) | € 1240/1 g (Inochem) | 63% | 100% | 49% | 31% |
| Pyro-PEG-FA (Formula I) | € 1280/1 g (Boc Sciences) | 92% | 90% | 69% | 57% |

Surprisingly, the synthesis process described above made it possible to obtain the compound of formula (I) with a total yield two times greater compared with the compound of You et al. The synthesis of the compound of formula (I) is thus more industrially advantageous than the synthesis of the compound of You et al., in particular from an economic point of view.

Example 2: Photophysical Properties of the Pyro-PEG-FA Conjugate of Formula (I) According to the Invention, of the Pheo-PEG-FA Conjugate of You et al., and of the TPP-FA Conjugate of Schneider et al Materials and Methods The absorption spectra were measured with a UV-3600 double beam UV-visible spectrophotometer (Shimadzu, Marne La Vallée, France). The fluorescence spectra were measured with a Fluorolog FL3-222 spectrofluorimeter (Horiba Jobin Yvon, Longjumeau, France) equipped with a 450 W xenon arc lamp, with a thermostated (25° C.) cuvette holder compartment, with an R928 UV-visible photomultiplier (Hamamatsu, Japan) and with a liquid nitrogen-cooled InGaAs infrared detector (DSS-16A020L Electro-Optical System Inc, Phoenixville, PA, USA). The excitation beam is diffracted by a SPEX double-grating monochromator (1200 lines/mm blazed at 330 nm). The fluorescence was measured by the UV-visible detector via the SPEX double-grating emission monochromator (1200 lines/mm blazed at 500 nm). The production of singlet oxygen was measured by the infrared detector via the SPEX double-grating emission monochromator (600 lines/mm blazed at 1 µm) and a high-pass filter at 780 nm. All the spectra were measured using 4-face quartz cuvettes. All the emission spectra (singlet-oxygen fluorescence and luminescence) were related back to the same absorbance (less than 0.2) with the lamp and photomultiplier corrections.

The fluorescence quantum yield was determined by equation (1):

$$\phi_f = \phi_{f_o} \cdot \frac{I_f}{I_{f_o}} \cdot \frac{OD_0}{OD} \cdot \left(\frac{n}{n_0}\right)^2 \quad (1)$$

where $\Phi_f$ and $\Phi_{fo}$, $I_f$ and $I_{fo}$, OD and OD$_o$, n and n$_o$, are the quantum yields, the fluorescence intensities, the optical densities, and the refractive indices of the sample and of the reference respectively.

The reference used for the calculation of the fluorescence quantum yield is tetraphenylporphyrin in toluene with a $\varphi_{fo}$ of 0.11.

The quantum yield for singlet oxygen production is determined by equation (2):

$$\phi_\Delta = \phi_{\Delta_0} \cdot \frac{I}{I_0} \cdot \frac{OD_0}{OD} \quad (2)$$

where $\Phi_\Delta$ and $\Phi_{\Delta o}$, I and I$_o$, OD and OD$_o$ are the quantum yields for singlet oxygen production, the singlet oxygen production intensities and the optical densities of the sample and of the reference respectively.

The reference used for the calculation of the quantum yield for singlet oxygen production is Rose Bengal in ethanol with a $\varphi_{\Delta o}$ of 0.68.

The fluorescence lifetime experiments were carried out using, for the excitation, a pulsed laser diode emitting at 407 nm (LDH-P-C-400M, FWHM<70 ps, 1 MHz) coupled to a PDL 800-D pulse generator (PicoQuant GmbH, Berlin, Germany) and, for the detection, an SPCM-AQR-15 avalanche photodiode (EG & G, Vaudreuil, Canada) coupled to a high-pass filter at 650 nm.

The acquisition was carried out using a PicoHarp 300 module linked to a PHR-800 4-channel router (PicoQuant GmbH, Berlin, Germany). The fluorescence declines were recorded using the single photon counting method (Time Correlated Single Photon Counting TCSPC). The data were collected until 1000 accumulated counts in a channel were obtained, then analyzed using the TCSPC Fluofit software (PicoQuant GmbH, Berlin, Germany) based on an iterative reconvolution using a Levensberg-Marquandt algorithm which allows multiexponential declines to be obtained.

The singlet oxygen lifetime measurements were carried out with a Tempro-01 spectrophotometer (Horiba Jobin Yvon, Longjumeau, France) composed of a SpectraLED-415 pulsed excitation diode emitting at 415 nm, of a cuvette holder compartment, of an emission monochromator of Seya-Namioka type (600-2000 nm) and of an H10330-45 thermoelectrically regulated near infrared photomultiplier tube (Hamamatsu, Japan). The assembly is controlled by the FluoroHub-B counting module and the DataStation and DAS6 software (Horiba Jobin Yvon).

The emission spectra and the phosphorescence lifetime measurements were carried out with a Fluorolog FL3-22 spectrofluorimeter (Horiba Jobin Yvon, Longjumeau, France) equipped with a 450 W continuous xenon lamp, with a xenon flash lamp, with a thermostated (25° C.) cuvette holder compartment and with an R928 UV-visible photomultiplier (Hamamatsu, Japan). The assembly is controlled by the FluoroHub-B counting module. The FluorEssence software (Horiba Jobin Yvon) was used for the emission spectra; the DataStation and DAS6 software (Horiba Jobin Yvon) were used for the measurement of the phosphorescence lifetimes.

Results

The photophysical properties in ethanol are indicated in table 2 below.

Example 3: Light-Stability of the Pyro-PEG-FA Conjugate of Formula (I) According to the Invention, of the Pheo-PEG-FA Conjugate of You et al., and of the TPP-FA Conjugate of Schneider et al Materials and Methods A solution of PS-arm-folic acid (Pyro-PEG-FA of formula (I)) (0.45 mM) in DMSO (3 ml) was irradiated ($\lambda$=365 nm, 5 mW·cm$^{-2}$, Xe-Hg lamp, Lightningcure™ LC5 Hamamatsu) for 2 hours. 100 µl of solution were taken every 15 minutes and diluted in 1.9 ml of methanol. Each sample (40 µl) was analyzed by reverse-phase high performance liquid chromatography (RP-HPLC) on a Prostar HPLC instrument (Varian). The HPLC was carried out on a Pursuit 5-C$_{18}$ column (2.5 µm, 4.6×150 mm, Varian) using an acetonitrile/(water+0.1% TFA) gradient [10%:90%] to [0%:100%] over the course of 25 minutes, followed by an isocratic plateau of acetonitrile for 10 minutes, then a return to the initial conditions for 5 minutes. The percentage degradation was calculated by comparing the area of the peaks corresponding to the initial conjugate and to the degraded conjugate.

Results

The results are given in FIG. 2.

The compound of the invention Pyro-PEG-FA of formula (I) is very much more stable than the Pheo-PEG-FA compound of You et al. and the TPP-FA compound of Schneider et al. Indeed, after 2 hours of irradiation (120 min), the Pyro-PEG-FA compound of the invention exhibits 5% degradation, whereas the Pheo-PEG-FA and TPP-FA compounds are between 30 and 40% degraded.

TABLE 2

| Compound | $\varepsilon_{soret\ band}$ (L·mol$^{-1}$·cm$^{-1}$) | $\lambda_{QI}$ (nm) | $\varepsilon_{QI}$ (L·mol$^{-1}$·cm$^{-1}$) | $\phi_F$ (±0.02) | $\phi_\Delta$ (±0.05) | $\tau_F$ (±0.1 ns) | $\tau_\Delta$ (±1 µs) |
|---|---|---|---|---|---|---|---|
| Pyro(a)-COOH | 76 326 | 668 | 33 265 | 0.34 | 0.52 | 6.7 | 13 |
| Pyro-PEG-FA | 74 081 | 668 | 35 306 | 0.30 | 0.54 | 6.4 | 13 |
| Pheo(a)-COOH | 69 663 | 667 | 32 537 | 0.44 | 0.52 | 5.7 | 12 |
| Pheo-PEG-FA | 49 215 | 667 | 22 870 | 0.40 | 0.48 | 5.7 | 13 |
| TPP-FA | 152 245 | 643 | 3 265 | 0.11 | 0.58 | 9.7 | 15 |

$\varepsilon$: molar extinction coefficient; Q: Q band; $\lambda_{exc}$: excitation wavelength; $\phi_f$: fluorescence quantum yield; $\phi_\Delta$: luminescence quantum yield; $\tau_f$: fluorescence lifetime; $\tau_\Delta$: singlet oxygen lifetime.

The compound of the invention Pyro-PEG-FA of formula (I) exhibits an absorption greater than that of the Pheo-PEG-FA compound of You et al. In particular, the molar extinction coefficient ($\varepsilon_{QI}$) at the excitation wavelength used clinically (668 nm) is 1.5 times greater.

The compound of the invention Pyro-PEG-FA of formula (I) exhibits an absorption greater than that of the TPP-FA compound of Schneider et al. In particular, the compound of the invention has an absorption peak at 668 nm that is more favorable to better penetration than the TPP-FA compound (absorption peak at 643 nm). In addition, the fluorescence quantum yield ($\phi_F$) and the molar extinction coefficient ($\varepsilon_{QI}$) are respectively approximately three times and ten times greater for the compound of the invention.

In conclusion, the compound of the invention Pyro-PEG-FA of formula (I) has improved photophysical properties in terms of absorption compared with the Pheo-PEG-FA compound of You et al. and the TPP-FA compound of Schneider et al.

In view of its good light-stability, the compound of the invention Pyro-PEG-FA of formula (I) is thus more suitable for photodynamic therapy applications.

Example 4: In Vitro Biological Evaluation 4.1. Impact of the Photodynamic Therapy on Tumor Cells and the Secretome Thereof Materials and Methods I. Cell Culture The SKOV-3 and OVCAR-3 ovarian tumor lines were purchased from the American Type Culture Collection (ATCC). The SKOV-3 cells were cultured in 50% DMEM (4.5 g/L D-glucose, L-glutamine; Gibco) and 50% F-12 (Ham's F-12 Nutrient Mix, Gibco), the OVCAR-3 cells were cultured in RPMI-1640 containing 1% 2 mM L-glutamine, 0.02 mM of sodium pyruvate, 100 U/ml of penicillin, 100 µg/ml of streptomycin and 10% of decomplemented fetal calf serum (Gibco).

II. Photodynamic Therapy

One million cells were deposited in a 25 cm$^2$ flask; after 24 h, the complete medium was replaced with a medium containing the compound of the invention Pyro-PEG-FA of formula (I) (PS) (1 mg per 100 ml of medium). After 24 h, the medium containing the PS was replaced with a complete medium after two rinses with PBS (Gibco BRL, Invitrogen, GB). Finally, the cells were subjected to the laser at a specific wavelength (668 nm) for one hour. 24 h later, the supernatant was recovered, centrifuged to remove the tumor cells in suspension, then frozen at −20° C. Three controls were used: nontreated SKOV-3 and OVCAR-3 tumor cells (NT), cells brought into contact with the PS but without illumination (+PS), cells illuminated only (+illu) and cells subjected to the PDT (PDT).

III. PBMC Isolation

The peripheral blood mononuclear cells (PBMCs) were isolated from a blood sample diluted in one volume of sterile PBS (Gibco BRL, Invitrogen, GB) and deposited on a Ficoll-Paque™ Plus (Amersham Biosciences AB, Sweden) density gradient. After centrifugation for 40 min at 400 g without deceleration, the ring of mononuclear cells was recovered, washed twice in PBS (300 g, 10 min) and then filtered.

IV. Real-time Quantitative PCR

1. RNA Extraction

The extraction of the RNAs from NK cells, B lymphocytes, CD4+ lymphocytes, regulatory T lymphocytes (Treg) and CD8+ lymphocytes was carried out from a dry pellet of $2\times10^5$ cells with the RNeasy Plus Mini extraction Kit (Qiagen, Hilden, Germany), according to the manufacturer's instructions. 30 µl of RNAse/DNase-free water (UltraPure Distilled Water, Gibco BRL, Invitrogen, GB) were used for the RNA elution. The SKOV-3, OVCAR-3 and PBMC RNA extraction was carried out from a pellet of $10^6$ cells dissolved in 1 ml of trizol (Invitrogen, New Zealand), according to the manufacturer's instructions. The pellet was solubilized in 10 µl of RNAse/DNase-free water. The RNA quantification was carried out by spectrophotometry (Ultraspec 3100 Pro, Amersham Biosciences, USA). The total RNA was stored at −80° C. 1% agarose gel electrophoresis (UltraPure Agarose, Invitrogen, USA) makes it possible to verify the integrity of the RNAs extracted.

2. Reverse Transcription

The Superscript II Reverse Transcriptase kit was used for the RT (Gibco BRL, Invitrogen, GB). The cDNA was synthesized from 2 µg/µl of total RNA, in a volume of 15 µl of water. 5 µl of the following mixture were then added: 1 µl of oligo dT (Roche, France)+0.1 µl of RNAsin 40 U/µl (Promega, USA)+4 µl of RNAse/Dnase-free water. After 10 min at 70° C. then 5 min at AT, 10 µl of a second mixture containing: 6 µl of 5X buffer (Tris-HCl, KCl, $MgCl_2$, Invitrogen, GB)+1 µl of DiThioThreitol (Invitrogen, GB)+2 µl of 10 mM dNTPs (Amersham Biosciences, GB)+0.1 µl of RNAsin (Promega, USA)+1 µl of Superscript II Reverse Transcriptase (Invitrogen, GB) were added. The sample was incubated for 1 h at 45° C. then 5 min at 95° C. The reaction was stopped by adding 70 µl of water/µg of initial RNA; the final concentration was 10 ng/µl.

3. Quantitative PCR

The principle is to monitor the neosynthesis of the DNA double strand, by virtue of measuring the incorporation of SybrGreen (fluorochrome which intercalates into the DNA). This reaction was carried out starting from cDNA at a concentration equivalent to 10 ng of RNA/µl of reaction mixture. The primers were designed and synthesized specifically for the Q-PCR (MWG-Biotech, Germany). The results were standardized using three housekeeping genes: 18S, GAPDH and HPRT (table 3 below).

The transcripts were quantified using Mx3005P (Stratagene, USA) in 96-well optical plates (Eurogentech, France). 10 µl of a pair of specific primers (10 pmol/µl) were deposited in each well, each plate containing the 44 pairs of primers and a control well containing $H_2O$, in duplicate. The Q-PCRs were carried out starting from 1 µl of cDNA sample (concentration equivalent to 10 ng of RNA/µl/well, according to the manufacturer's instructions with the Mesa Green qPCR MasterMix Plus for SYBR® Assay kit (Eurogentec, France). After a first denaturation for 5 minutes at 95° C., the reaction mixture was subjected to 45 amplification cycles consisting of a succession of passages of 15 s at 95° C. (denaturation of the DNA double strand) then of 1 minute at 60° C. (hybridization of the primers and elongation of the neosynthesized DNA strand). The fluorescence intensity was measured at the end of each elongation cycle and a melting cycle was programmed immediately after the final amplification. The simultaneous expression of the two isoforms of the folate receptor, FOLR1 and FOLR2, by the SKOV-3 and OVCAR-3 tumor cells was analyzed, as was the simultaneous expression of said isoforms by various immune cell lines such as PBMCs, Natural Killer (NK) lymphocytes, B lymphocytes, CD4+ lymphocytes, CD8+ lymphocytes and regulatory T lymphocytes.

4. Analysis and Representation of the Results

The quantitative expression of a gene was interpreted using the ΔCT method. The gene expression is given as "CT" (Cycle Threshold) then standardized by the mean of the three housekeeping genes=ΔCT. The experiments were carried out in duplicate.

TABLE 3

Summary of the primers

| | Forward and reverse primer | |
|---|---|---|
| FOLR1 | 5'-AGGTGCCATCTCTCCACAGT | 5'-GAGGACAAGTTGCATGAGCA |
| FOLR2 | 5'-CTGGCTCCTTGGCTGAGTTC | 5'-GCCCAGCCTGGTTATCCA |
| 18S | 5'-TCAAGAACGAAAGTCGGAGG | 5'-GGACATCTAAGGGCATCACA |
| GAPDH | 5'-GCCAAGGTCATCCATGACAACTTTGG | 5'-GCCTGCTTCACCACCTTCTTGATGTC |
| HPRT | 5'-CCCTGGCGTCGTGATTAG | 5'-ATGGCCTCCCATCTCCTT |

V. Viability Test

On the tumor cells: 2000 tumor cells (SKOV-3 and OVCAR-3) were placed in a white-bottomed 96-well plate (Falcon®) in 100 µl of their corresponding medium (DMEM/F-12 and RPMI). The cells were activated with 1 µl/ml of anti-CD3 antibody (Ab), previously applied on the plates (2 h at 37° C.), and 1 µl/ml of anti-CD28 antibody. The culturing is carried out according to a time course of 3 h, 24 h, 72 h and 120 h, then a viability test was carried out for each time. This test makes it possible to quantify ATP present in the cells by virtue of the luciferase reaction for determining the number of cells viable in culture.

On the immune cells: $10^5$ PBMCs were cultured with 50% of ML10 (50 µl) and 50% of supernatant from the tumor cells, subjected to the various conditions (nontreated, PS only, illumination only and subjected to the PDT), collected beforehand (50 µl).

VI. Proliferation Assay $10^5$ PBMCs were cultured in round-bottomed 96-well plates (BD Falcon®), in 50 μl of culture medium: RPMI-1640, 1% 2 mM L-glutamine, 0.02 mM of sodium pyruvate, 100 U/ml of penicillin, 100 μg/ml of streptomycin, 10% of decomplemented human AB serum (GIBCO BRL, Invitrogen, GB) and 50 μl of the supernatant from the tumor cells according to the various conditions (NT, PS only, illumination only and PDT). The cells were activated with 1 μg/ml of anti-CD3, previously deposited on the plates (2 h at 37° C.), and 100 ng/ml of anti-CD28. The proliferation was evaluated by incorporation of 1 μCi/well of tritiated thymidine ($^3$H-Th) (GE Healthcare, France), 18 h before the end of the culture. According to a time course of 24 h, 48 h, 72 h and 120 h, the plates were filtered and the filters were read in a radioactivity counter (1450 Trilux, Wallac, Finland). The experiments were carried out in triplicate and the results are expressed in counts per minute (cpm).

VII. Flow Cytometry

The anti-human monoclonal antibodies used were coupled to fluorochromes (see table 4 below). For the control, an isotype of the various monoclonal antibodies was used as control. $10^5$ cells were taken up in a volume of 100 μl of sterile PBS and incubated with 5 μl of each Ac (10 min at ambient T° (AT) and in the dark). The labeled cells were washed by adding 200 μl of PBS then centrifuging for 5 minutes at 600 g; the supernatant was then discarded. The cells were then taken up in 200 μl of PBS and, finally, analyzed by flow cytometry (BD FACSCanto-II).

TABLE 4

Representation of the various anti-human monoclonal antibodies used for the flow cytometry.

| Antibodies | Isotypes |
|---|---|
| CD4 (VIT4)-VioBlue | IgG2a (mouse)-VioBlue |
| CD8-VioGreen | IgG2a (mouse)-VioGreen |
| CD19-VioBright FITC | IgG1 (mouse)-VioBright FITC |
| CD14-PE | IgG2a (mouse)-PE |
| CD3-PE-Vio770 | IgG2a (mouse)-PE-Vio770 |
| CD335 (NKp46)-APC | IgG1 (mouse)-APC |
| CD11C-APC-Vio770 | IgG2b (mouse)-APC-Vio770 |
| CD4 (VIT4)-VioBlue | IgG2a (mouse)-VioBlue |
| CD30-APC-Vio770 | IgG1 (mouse)-APC-Vio770 |
| CD69-PE-Vio770 | IgG1 (mouse)-PE-Vio770 |
| Anti-HLA-DR-PerCP-Vio700 | IgG2a (mouse)-PerCP-Vio700 |
| CD152-APC | IgG2a (mouse)-APC |
| CD197 | REA Control (S)-PE |
| CD25-VioBright FITC | IgG2b (mouse)-VioBright FITC |
| CD8-VioGreen | IgG2a (mouse)-VioGreen |
| CD4 (VIT4)-VioBlue | IgG2a (mouse)-VioBlue |
| CD25-VioBright FITC | IgG2b (mouse)-VioBright FITC |
| CD127-PE-Vio770 | IgG2a (mouse)-PE-Vio770 |
| CD4 (VIT4)-VioBlue | IgG2a (mouse)-VioBlue |
| CD18-FITC | IgG1 (mouse)-FITC |
| CD223-PE | REA Control (S)-PE |
| CD49b-PE-Vio770 | REA Control (S)-PE-Vio 770 |
| CD152-APC | IgG2a (mouse)-APC |

Results

The transcriptome analysis showed that the ovarian tumor cell lines studied (SKOV-3 and OVCAR-3) preferentially expressed the FOLR1 isoform, thus showing their potential sensitivity with respect to the new photosensitizer of the invention, Pyro-PEG-FA of formula (I), and thus their sensitivity to photodynamic therapy (PDT)-induced death.

At the end of the PDT, the in vitro morphological analysis of the SKOV-3 and OVCAR-3 ovarian tumor cells showed that they were sensitive to the PDT with a visible effect as early as one hour post-illumination (not adherent cells, appearance of cell lysis). These results were supported by a viability test (MTT) on the ovarian tumor cells subjected in vitro to the photodynamic therapy. Indeed, it was observed that the SKOV-3 and OVCAR-3 ovarian tumor cells subjected to the PDT exhibited a significant decrease in their cell viability over time. On the other hand, it was observed that there was no notable modification of the viability of the nontreated tumor cells or tumor cells subjected only to the PS or to the illumination. Thus, these results validate the efficacy of the PS of the invention, Pyro-PEG-FA of formula (I), and show that the PDT is indeed capable of inducing ovarian tumor cell death with a very rapid effect, since 90% of the tumor cells are dead after only one hour of illumination (FIG. 3A).

The impact of the secretome of the ovarian tumor cells subjected to the PDT on the human peripheral blood mononuclear cells (PBMCs) was studied. The PBMCs, cultured with supernatant from OVCAR-3 or from SKOV-3 subjected to the PDT, showed an increase in their viability after only 3 hours of culture. This increase in mitochondrial metabolism was obtained in three independent experiments and is statistically significant (at 48 h and 120 h). These results thus illustrate that PDT using this new photosensitizer Pyro-PEG-FA of formula (I) can modify the secretome of tumor cells in favor of a secretome which activates human immune cell proliferation.

The effect of the secretome of the SKOV-3 tumor cells subjected to the PDT on the phenotype of the immune populations was analyzed. For that, the expression of the markers of the various immune populations was analyzed by flow cytometry. The results obtained showed that the secretome of the SKOV-3 tumor cells did not induce any modification of the percentage of CD4+ T and CD8+ T lymphocytes, monocytes, B lymphocytes or NK cells in the PBMCs, regardless of the culture conditions. Moreover, the early and late activation markers were specifically analyzed in the CD4+ T cells, and the results showed that the secretome of the ovarian tumor cells subjected to the various treatments also did not induce any modification of the CD4+ T activation. Thus, contrary to radiotherapy or chemotherapy, all of the results obtained showed that PDT using the new photosensitizer Pyro-PEG-FA of formula (I) did not impair the quality of antitumor effector immune response.

The impact of the secretome of the SKOV-3 cells subjected to the PDT on the populations of natural regulatory T lymphocytes and induced regulatory T lymphocytes (Tr1) was also studied. The analysis of the results obtained (by analyzing the Tr1 on the basis of the triple labelings CD4+CD18+CD49b or CD4+CD49b+LAG3+) showed that the secretome of the nontreated SKOV-3 cells induces Tr1-type populations. Surprisingly, it was observed that the various treatments (Illumination+, PS+ or PDT) do not promote this Tr1 induction. Thus, contrary to conventional radiotherapy, PDT using this new photosensitizer Pyro-PEG-FA of formula (I) does not modify the secretome of tumor cells in favor of an environment that is even more immunosuppressive, which would be favorable to the tumor escaping the immune system and thus to tumor progression.

4.2. Immune Cell Activation

The activation state of the various T lymphocyte populations, in particular the CD4+ (CCR7+, CD25, CD30, CD69, CTLA4 and HLADR) T lymphocytes (LTs) and the CD8+ (CCR7+, CD25, CD30, CD69, CTLA4 and HLADR) LTs, was analyzed by flow cytometry.

It is first of all observed, for the CD4+ LTs, that the CD69+ marker (early activation marker) is present from 24 hours up to 72 hours. PDT allows a greater expression of the CD69+ marker than the cells that were not treated. With regard to the illumination alone or photosensitizer (Ps) alone conditions, the results do not show any major variation compared with the nontreated cells.

For the CD8+ LTs, the CD69+ marker is present from 24 hours up to 120 hours. The cells subjected to PDT allow an increase in the expression of the CD69+ marker, which is an early activation marker, since the fluorescence median is greater than for the nontreated cells. With regard to the ILL alone or Ps alone conditions, the results do not show any major variation compared with the nontreated cells.

Thus, these results suggest that the ovarian carcinomatosis cells subjected to PDT produce factors which promote the early activation of CD4+ and CD8+ T lymphocytes. A presence of the CTLA4+ marker (early activation marker) is observed for the CD4+ and CD8+ LTs from 24 hours to 72 hours. It is noted that the median fluorescence is greater in the two cases for the cells subjected to PDT compared with the nontreated cells. This indicates that the media conditioned by the cancer cells subjected to PDT make it possible to potentiate an expression of the marker on CD4+ LTs and CD8+ LTs.

The illuminated condition allows a strong increase in the expression of this marker.

With regard to the Ps alone condition, it is observed that the expression of the CTLA4+ marker is always lower than the nontreated cells. After 72 hours, with the PDT condition, the expression of the CTLA4+ marker is lost, and said marker is replaced by the HLADR+marker (activation marker associated with antigen presentation) both for the CD4+ LTs and for the CD8+ LTs. Thus, our results suggest that PDT indirectly promotes the expression (i) of HLADR, which is favorable to immune activation, and (ii) of CTLA4 initially, then a decrease in the expression of this marker is observed. This result is consistent since CTLA4 is considered later during the immune response, as an immune check point, that is to say as a point of negative feedback of the immune response.

At 24 hours, an increase in the expression of the CD30+ marker (late activation marker) is observed essentially for the cells subjected to PDT; this is the case for the CD4+ LTs at 48 hours. On the other hand, for the CD8+ LTs, the PDT condition allows an overexpression of the CD30+ marker, which is then followed by an overexpression of the CD25+ marker (activation marker and IL-2 R-alpha receptor). After 72 hours, the CD30+ activation marker decreases on the CD4+ LTs in the PDT condition/nontreated condition. On the other hand, for the CD8+ LTs, the expression of the CD30+ marker is very high in the PDT condition. After 120 hours, the expression of the CD25+ marker is increased in the two cases CD4+ LT and CD8+ LT for the cells in the PDT condition. Thus, all of these results suggest that the ovarian carcinomatosis cells subjected to PDT produce factors which promote CD4+ and CD8+ T lymphocyte activation.

After 48 h and up to 120 hours of culture, an increase is observed in the expression of the CCR7+ marker (CCL19 and CCL21 chemokine receptor) both for the CD4+ LTs and for the CD8+ LTs. The expression of the marker is in general greater for the cells subjected to PDT. The PDT thus allows the expression of the CCR7+ marker which is a chemokine receptor involved in immune cell lymph node migration. It should be noted that the illumination alone itself also allows a considerable increase in the expression of this CCR7+ marker. Thus, these results suggest that the ovarian carcinomatosis cells subjected to PDT produce factors capable of promoting CD4+ and CD8+ T lymphocyte migration via the CCL19 and 21 chemokines.

The inventors have thus shown, by flow cytometry, that the conditioned media induce not only a clonal expansion of the immune cells, but also an increase in a certain number of activation markers over time (early or late), suggesting that the immune cells are effector cells, namely that the immune cells have an activated phenotype making it possible to ensure an antitumor effect.

4.3. Impact on Cytokine Secretion

Immunoassays were carried out on the supernatant of the OVCAR-3 ovarian carcinomatosis tumor cells treated by PDT in order to determine whether the supernatants from the tumor cells express and release cytokines after the PDT treatment.

Method

A sandwich ELISA assay was carried out. Firstly, the primary antibody specific for the cytokine being sought is bound to a support overnight at 4° C. The following day, washing with PBS-0.05% Tween makes it possible to remove the nonbound antibodies. In order to prevent absorption of other, nonspecific, molecules on the support, a saturation is performed by coating the free zones with a molecule (in this case bovine serum albumin (BSA)) which has no affinity with the variable and specific zones of the primary antibody. Washing is then carried out in order to remove the molecules in suspension, before the addition of the sample. If the cytokine being sought is present, an immune complex forms with the primary antibody which is specific for said immune complex. The possible nonspecific molecules present remain in suspension. Washing makes it possible to remove the nonbound elements. The final step consists in adding the secondary antibody specific for the cytokine. The visualization is carried out by means of an enzyme, peroxidase, which converts a chromogenic substrate (ortho-phenylenediamine) into a chromophore product which is quantifiable on a spectrophotometer. This enzyme is coupled to streptavidin. By virtue of the biotin, present on the secondary antibody, which has a strong affinity for streptavidin, the biotin/streptavidin/peroxidase complex forms, allowing the quantification. To stop the enzymatic reaction, a diacid (in this case HCl) is added.

Results

The results are presented in FIG. 3B.

Interleukin 6 (IL6)

IL6 is a pro-inflammatory cytokine, that is to say that it is capable of promoting inflammatory processes, which is not beneficial since, in this cancer in particular, the production of inflammation promotes tumor progression and the dissemination of metastasis. The results show that, for the nontreated control Ovcar-3 cells (NT), an IL6 cytokine concentration of 53.45 pg/ml, which is a large amount, is observed. For the illuminated Ovcar-3 cells, a strong decrease in the cytokine (9.06 pg/ml) is observed compared with the nontreated cells, thereby making it possible to deduce that the illumination of the Ovcar-3 ovarian cancer cells subjected to illumination for one hour leads to the decrease in the presence of IL6 cytokines, which is very encouraging. The Ps alone allows a decrease (29.08 pg/ml) in the IL6 cytokine. For the test Ovcar-3 cells that were treated by PDT, a decrease (19.12 pg/ml) is observed compared with the nontreated cells (53.45 pg/ml).

Thus, these results suggest that the Ovcar-3 cells treated by PDT decrease their IL6 cytokine production. These first results are very favorable with regard to the use of PDT as an antitumor treatment.

Interleukin 2 (IL2)

IL2 plays a major role in immune response homeostasis, by promoting the survival and proliferation in particular of T lymphocytes. For the nontreated Ovcar-3 cell control condition (NT), a presence of IL2 with a concentration of 72.50 pg/ml is detected. On the other hand, for the ILL and Ps conditions, IL2 cytokine is no longer observed, with a concentration equal to 0 pg/ml. The cells treated by illumination alone and the cells in contact with the Ps alone thus cause a considerable decrease in IL2 cytokine secretion. For the Ovcar-3 cells subjected to PDT, the inventors observed an increase in IL2 production (122.50 pg/ml) compared with the nontreated cells, thereby showing that the treatment by PDT is in favor of LT proliferation.

Thus, these results show that PDT promotes IL-2 secretion by the ovarian carcinomatosis cells, which is in favor of a proliferative effect on the immune cells and on the LTs in particular. This result correlates with the increase in expression of CD25 on CD4+ and CD8+ LTs (see cytometry results).

Interferon Gamma (IFN-Gamma)

For the control condition, with the nontreated cancer cells, a concentration of 2.72 pg/ml of IFN-gamma is detected. The Ovcar-3 cells treated by illumination allow a very slight increase (2.85 pg/ml) in this cytokine. On the other hand, for the Ovcar-3 cells in contact with Ps alone, IFN-gamma is not detectable, which means that Ps alone leads to the elimination of this cytokine. For the test condition (cells subjected to PDT), a strong increase (28.55 pg/ml) in IFN-gamma is observed.

These results indicate that PDT is capable of promoting IFN-gamma production by the ovarian carcinomatosis cells and thus of contributing to an antitumor effect via this cytokine. Indeed, IFN-gamma makes it possible to prevent the development of malignant tumors and of metastases in particular by inhibiting angiogenesis, by stimulating the B and T lymphocyte maturation, but also by activating other immune cell types, such as monocytes.

TGF-Beta

The nontreated cancer cells produce TGF-beta at a concentration of 28.94 pg/ml. The "Ovcar-3 cells treated by illumination" condition shows a decrease in the cytokine concentration (8.95 pg/ml), which is encouraging. On the other hand, for the Ovcar-3 cells in contact with only PS, a considerable increase in the cytokine concentration (49.56 pg/ml) is observed. For the PDT condition, it is observed that the concentration has literally dropped (1.36 pg/ml).

Thus, the results obtained suggest that PDT decreases the production of the immunosuppressive cytokine TGF-beta by the ovarian carcinomatosis cells. This effect is beneficial since it makes it possible to limit the immunosuppressive microenvironment which is favorable to tumor growth.

Conclusion

The inventors studied the impact of the supernatant of ovarian cancer cells subjected to PDT, on peripheral blood mononuclear cells. They studied the state of activation of the various T lymphocyte populations, in particular CD4+ LTs and CD8+ LTs. The results showed that the Ovcar-3 cells subjected to PDT are capable of activating CD4+T and CD8+ T lymphocytes. An increase in CD69+, CTLA4+, CCR7+, CD30+, CD25+ and HLADR+ activation markers was thus observed.

The inventors also investigated the potential cytokine production after treatment of the Ovcar-3 cells by PDT. The results observed show that the tumor cells subjected to PDT allow a decrease in pro-inflammatory cytokines such as IL6 and a decrease in the presence of TGF-beta which is immunosuppressive. The results also made it possible to reveal an increase in cytokines favorable to immune cell survival and proliferation and activation, such as the IL2 and IFN-gamma cytokines.

The ovarian tumor cell PDT products promote the Th1 pathway (cellular immunity pathway), which is in particular favorable to the antitumor immune response. Furthermore, they do not activate the inflammatory or regulatory pathways.

Example 5: In Vivo Study

I. Rat Ovarian Carcinoma: NuTu-19 Cell Line

The NuTu-19 cell line was a rat syngenic ovarian adenocarcinoma line which allows the ovarian tumor development in an immunocompetent rat (Rose et al., Am. J. Obstet. Gynecol. 1996, 175(3 Pt 1), 593-9). The cells were stored in liquid nitrogen ($5 \times 10^6$ cells per cryotube) then cultured in DMEM (Gibco-Life Technologies™) supplemented with 10% of decomplemented fetal calf serum and 1% of penicillin/streptomycin mixture and 1% of glutamax. The cells were incubated under standardized conditions (5% $CO_2$, 100% humidity, 37° C.). When the cells were at confluence, they were trypsinized in order to lift the adhesion and to allow them to be collected (0.25% trypsin solution, Gibco-Life Technologies™), washed with PBS (Dulbecco's phosphate buffered saline, Gibco-Life Technologies™) and counted after a trypan blue exclusion test in order to evaluate viability. The cells were injected intraperitoneally, in the form of a cell suspension in PBS, into various rats in order to obtain a peritoneal carcinomatosis model.

II. Animal Model of Peritoneal Carcinomatosis

A validated peritoneal carcinomatosis model (Rose et al., Am. J. Obstet. Gynecol. 1996, 175(3 Pt 1), 593-9) was used. Female Fisher F344 rats were obtained from the supplier Harlan®. The animals were housed in the animal house of the Département Hospitalo-Universitaire de Recherche Expérimentale [Hospital-University Experimental Research Department] (DHURE—University of Medicine Research Pole—CHRU of Lille). The feed (SAFE™) and water were supplied ad libitum.

The carcinomatosis level was obtained by intraperitoneal inoculation of an NuTu-19 cell suspension in PBS ($20 \times 10^6$ cells per rat). The rats were monitored regularly until the development of ascites occurred, attesting to tumor progression, or until an exploratory celioscopy was performed, intended to confirm the presence of peritoneal carcinomatosis lesions.

The expression of the folate receptor by the NuTu-19 cell line and the carcinomatosis lesions was confirmed by Azaïs et al.(Int J Gynecol Cancer 2015).

The in vivo fluorescence measurements were carried out 4 hours after the administration of the photosensitizer at the dose of 4 mg/kg intraperitoneally. The detection protocol was carried out immediately after anesthesia with isoflurane, celioscopically, in order to visualize the fluorescence emitted by the carcinomatosis lesions (photodiagnosis).

III. Photodiagnosis

The Pyro-PEG-FA compound of formula (I) was detected by fluorescence with the Olympus® medical celioscopy device (Evis Exera II), which has a PDD (photodiagnosis) function. The celioscopy optic used was a 4 mm Olympus® cystoscope having a viewing angle of 30°.

The PDD function was developed by Olympus® for the diagnosis of bladder tumors not visible under white light (in situ carcinomas, dysplasias, small focal tumors). The administration of a protoporphyrin IX precursor (PpIX), 5-aminolevulinic acid (5-ALA) and more recently hexyl aminolevulinate (HAL, Hexvix®) has made it possible to specifically visualize the bladder lesions which appear fluorescent (red) under blue light.

The light source was a Xenon source. A first filter system allowed blue light excitation between 380 and 440 nm. A yellow second filter made it possible to accentuate the contrast between the blue light and the red fluorescence emitted between 625 and 655 nm, given that this filter enabled the optimal observation of a fluorescence emitted around 640 nm. Since the red fluorescence emitted by the PpIX is too weak compared with the blue light, this yellow filter was inserted at the level of the camera in order to accentuate the contrast between the blue and the red and to allow good visualization of the lesions.

Four hours after the intraperitoneal injection, a general anesthetic was administered by continuous inhalation of isoflurane (concentration ranging from 1.5% to 3%). An open celioscopy was performed on the median line allowing the introduction of a 5 mm trocar. A purse string suture was inserted with Vicryl© 2.0 in order to maintain the leaktightness around the trocar. The insufflation was put in place on the tap of this trocar with a flow rate of 0.2 l/min of $CO_2$, making it possible to obtain a constant pneumoperitoneum of 3 mmHg. The introduction of a 5 mm celioscope through this trocar made it possible to explore the peritoneal cavity, first under white light then under blue light.

The procedure was carried out on three rats after intraperitoneal administration of the PS at the dose of 4 mg/kg.

FIG. 4A represents the celioscopy image obtained in an immunocompetent rat having developed a peritoneal carcinomatosis after IP injection of NuTu-19 cells (rat syngenic ovarian adenocarcinoma cell line). The carcinomatosis lesion appears in white. FIG. 4B corresponds to FIG. 4A under white light.

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: FOLR1 forward

<400> SEQUENCE: 1
aggtgccatc tctccacagt                                           20

<210> SEQ ID NO 2
<211> LENGTH: 20
<212> TYPE: DNA
<213> ORGANISM: Artificial Sequence
<220> FEATURE:
<223> OTHER INFORMATION: FOLR1 reverse

<400> SEQUENCE: 2
gaggacaagt tgcatgagca                                           20

<210> SEQ ID NO 3
<211> LENGTH: 20
<212> TYPE: DNA
<213> ORGANISM: Artificial Sequence
<220> FEATURE:
<223> OTHER INFORMATION: FOLR2 forward

<400> SEQUENCE: 3
ctggctcctt ggctgagttc                                           20

<210> SEQ ID NO 4
<211> LENGTH: 18
<212> TYPE: DNA
<213> ORGANISM: Artificial Sequence
<220> FEATURE:
<223> OTHER INFORMATION: FOLR2 reverse

<400> SEQUENCE: 4
gcccagcctg gttatcca                                             18

<210> SEQ ID NO 5
<211> LENGTH: 20
<212> TYPE: DNA
<213> ORGANISM: Artificial Sequence
<220> FEATURE:
```

<223> OTHER INFORMATION: 18S forward

<400> SEQUENCE: 5
tcaagaacga aagtcggagg                                                    20

<210> SEQ ID NO 6
<211> LENGTH: 20
<212> TYPE: DNA
<213> ORGANISM: Artificial Sequence
<220> FEATURE:
<223> OTHER INFORMATION: 18S reverse

<400> SEQUENCE: 6
ggacatctaa gggcatcaca                                                    20

<210> SEQ ID NO 7
<211> LENGTH: 26
<212> TYPE: DNA
<213> ORGANISM: Artificial Sequence
<220> FEATURE:
<223> OTHER INFORMATION: GAPDH forward

<400> SEQUENCE: 7
gccaaggtca tccatgacaa ctttgg                                             26

<210> SEQ ID NO 8
<211> LENGTH: 26
<212> TYPE: DNA
<213> ORGANISM: Artificial Sequence
<220> FEATURE:
<223> OTHER INFORMATION: GAPDH reverse

<400> SEQUENCE: 8
gcctgcttca ccaccttctt gatgtc                                             26

<210> SEQ ID NO 9
<211> LENGTH: 18
<212> TYPE: DNA
<213> ORGANISM: Artificial Sequence
<220> FEATURE:
<223> OTHER INFORMATION: HPRT forward

<400> SEQUENCE: 9
ccctggcgtc gtgattag                                                      18

<210> SEQ ID NO 10
<211> LENGTH: 18
<212> TYPE: DNA
<213> ORGANISM: Artificial Sequence
<220> FEATURE:
<223> OTHER INFORMATION: HPRT reverse

<400> SEQUENCE: 10
atggcctccc atctccett                                                     18

The invention claimed is:
1. A compound of formula (I):

(I)
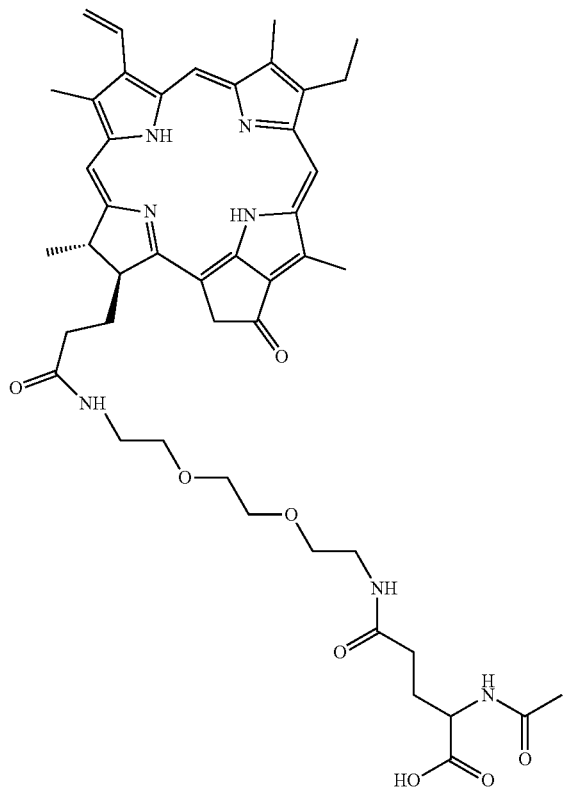
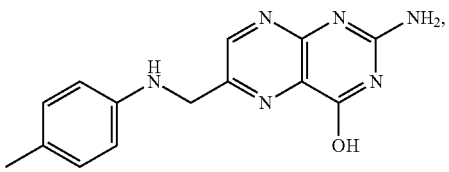

or a pharmaceutically acceptable salt thereof.

2. A medicament, comprising the compound of claim 1, or a pharmaceutically acceptable salt thereof.

3. A method of treating cancer, comprising the step of administrating the compound of claim 1, or a pharmaceutically acceptable salt thereof, to a patient in need thereof.

4. The method as claimed in claim 3, wherein the compound is used in the treatment of cancer by photodynamic therapy.

5. The method as claimed in claim 3, wherein risk of developing metastases is reduced.

6. The method as claimed in claim 3, wherein the cancer is ovarian cancer, lung cancer, kidney cancer, endometrial cancer, colorectal cancer, breast cancer, pancreatic cancer, brain cancer, gastric cancer, liver cancer, prostate cancer, testicular cancer, bladder cancer, or head and neck cancer.

7. The method as claimed in claim 6, wherein the cancer is ovarian cancer.

8. The method as claimed in claim 3, wherein said method comprises intraperitoneal or intravenous administration of the compound of claim 1, or a pharmaceutically acceptable salt thereof.

9. A process for preparing a compound of formula (I):

(I)
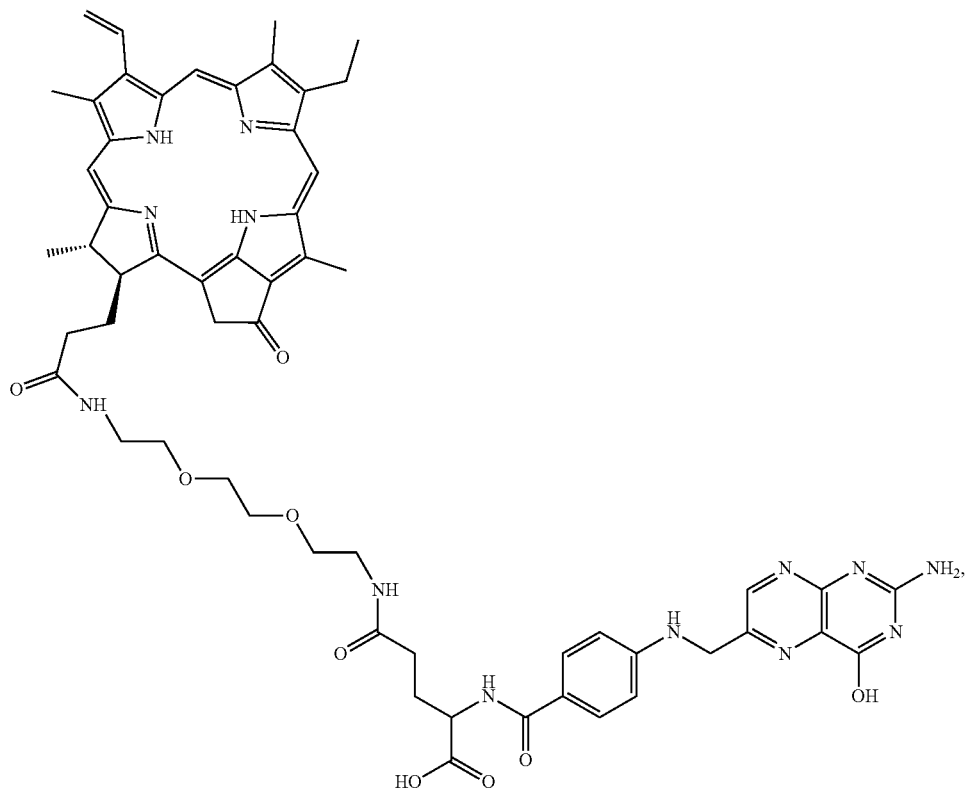

wherein that the process comprises a step of coupling between a compound of formula (II):
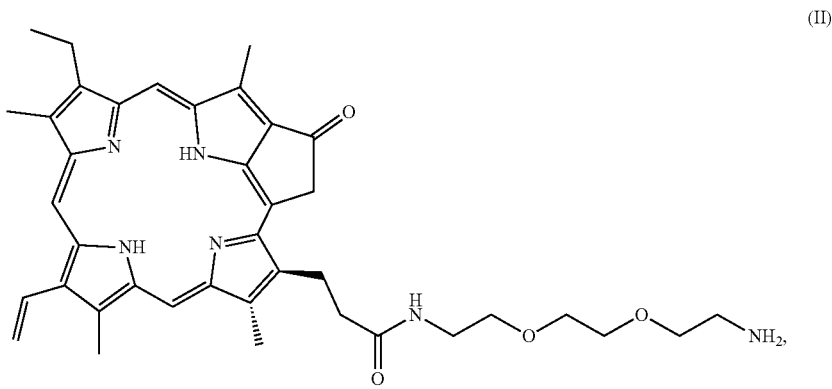
(II)
and folic acid.
10. The process as claimed in claim 9, comprising the following steps:
(a) a step of coupling between a compound of formula (IV):
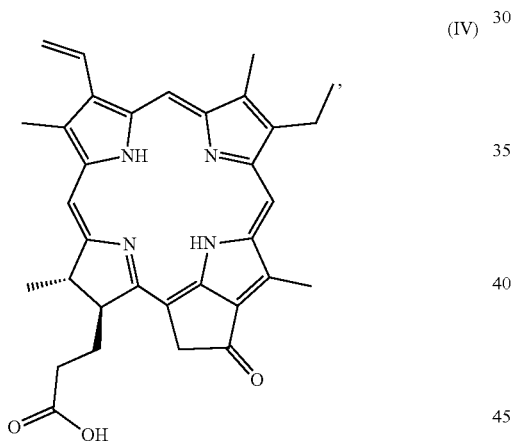
(IV)
and N-Boc-2,2'-(ethylenedioxy)diethylamine, so as to obtain a compound of formula (III):
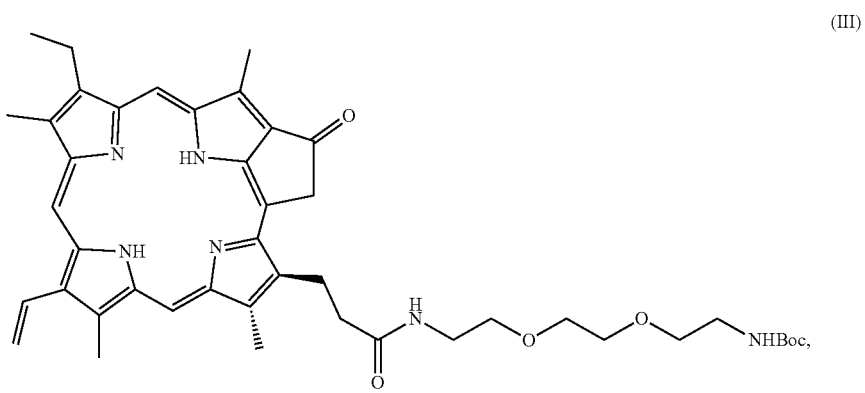
(III)

b) a step of deprotection of the compound of formula (III) obtained in step a) so as to obtain a compound of formula (II):

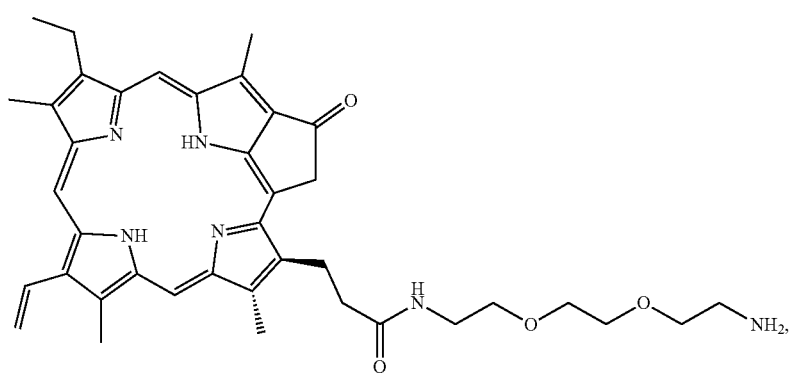

(II)

and c) a step of coupling between the compound of formula (II) obtained in step b) and folic acid so as to obtain a compound of formula (I):

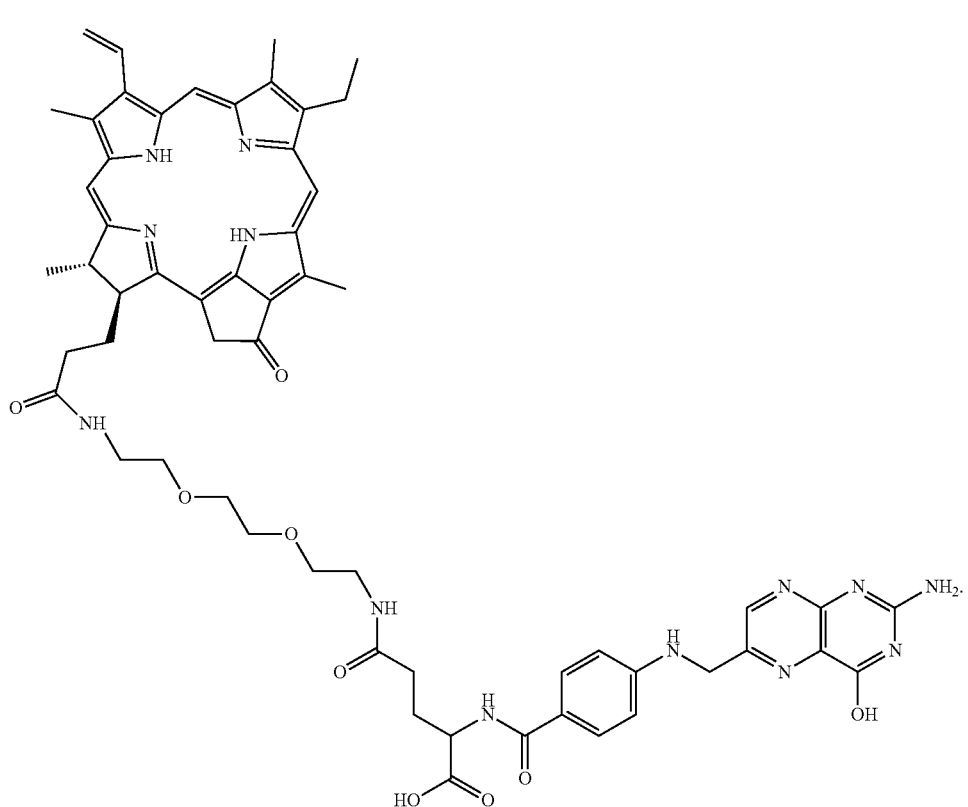

(I)

11. A fluorescent marker, comprising the compound of formula (I), or a pharmaceutically acceptable salt thereof.

12. A method for imaging in a subject, comprising the visualization of the fluorescence emitted by a compound of formula (I) as claimed in claim 1, said compound of formula (I) being previously administered to said subject and photoactivated by a light source.

* * * * *